(12) United States Patent
Beach et al.

(10) Patent No.: US 9,005,126 B2
(45) Date of Patent: Apr. 14, 2015

(54) ULTRASONIC TISSUE DISPLACEMENT/STRAIN IMAGING OF BRAIN FUNCTION

(75) Inventors: Kirk Beach, Seattle, WA (US); John C. Kucewicz, Seattle, WA (US); Barbrina Dunmire, Seattle, WA (US)

(73) Assignee: University of Washington, Seattle, WA (US)

( * ) Notice: Subject to any disclaimer, the term of this patent is extended or adjusted under 35 U.S.C. 154(b) by 1272 days.

(21) Appl. No.: 12/114,703

(22) Filed: May 2, 2008

(65) Prior Publication Data

US 2008/0275340 A1    Nov. 6, 2008

Related U.S. Application Data

(60) Provisional application No. 60/915,897, filed on May 3, 2007.

(51) Int. Cl.
*A61B 8/00* (2006.01)
*G06K 9/00* (2006.01)
*A61B 8/08* (2006.01)
*A61B 5/0402* (2006.01)

(52) U.S. Cl.
CPC ............. *A61B 8/0808* (2013.01); *A61B 8/0816* (2013.01); *A61B 5/0402* (2013.01)

(58) Field of Classification Search
USPC ................. 600/437–438, 442, 454–455, 465; 382/128
See application file for complete search history.

(56) References Cited

U.S. PATENT DOCUMENTS

| 5,088,498 A | 2/1992 | Beach et al. ................... 600/453 |
| 5,183,046 A | 2/1993 | Beach et al. ................... 600/453 |

(Continued)

FOREIGN PATENT DOCUMENTS

WO    WO 02/069805    9/2002    ............... A61B 8/06

OTHER PUBLICATIONS

Aaslid, R., "Visually Evoked Dynamic Blood Flow Response of the Human Cerebral Circulation", Stroke, 1987, 18:771-775.*

(Continued)

*Primary Examiner* — Katherine Fernandez
(74) *Attorney, Agent, or Firm* — Kilpatrick Townsend and Stockton LLP

(57) ABSTRACT

Tissue Pulsatility Imaging (TPI) is an ultrasonic technique developed to measure tissue displacement or strain in the brain due to blood flow over the cardiac and respiratory cycles. Such measurements can be used to facilitate the mapping of brain function as well as to monitor cerebral vasoreactivity. Significantly, because tissue scatters ultrasound to a greater extend than does blood, using ultrasound to measure tissue displacement or strain in the brain is easier to implement than using ultrasound to measure blood flow in the brain. Significantly, transcranial Doppler sonography (TCD) has been used to measure blood flow in the brain to map brain function and monitor cerebral vasoreactivity; however, TCD can only acquire data through the three acoustic windows in the skull, limiting the usefulness of TCD. TPI is not so limited.

32 Claims, 15 Drawing Sheets

(56) References Cited

U.S. PATENT DOCUMENTS

| | | | |
|---|---|---|---|
| 5,194,291 | A | 3/1993 | D'Aoust et al. ............... 148/276 |
| 5,289,820 | A | 3/1994 | Beach et al. ................... 600/443 |
| 5,534,232 | A | 7/1996 | Denes et al. ............. 422/186.26 |
| 5,638,823 | A | 6/1997 | Akay et al. ..................... 600/528 |
| 5,824,277 | A | 10/1998 | Campos ..................... 423/242.1 |
| 5,840,028 | A | 11/1998 | Chubachi et al. .............. 600/437 |
| 5,919,139 | A | 7/1999 | Lin ................................ 600/443 |
| 5,935,339 | A | 8/1999 | Henderson et al. ................. 134/1 |
| 5,951,476 | A * | 9/1999 | Beach ............................ 600/437 |
| 6,066,097 | A * | 5/2000 | Glenn et al. ................... 600/443 |
| 6,200,539 | B1 | 3/2001 | Sherman et al. .......... 422/186.04 |
| 6,390,979 | B1 * | 5/2002 | Njemanze ...................... 600/438 |
| 6,406,759 | B1 | 6/2002 | Roth .............................. 427/562 |
| 6,626,855 | B1 | 9/2003 | Weng et al. ......................... 601/3 |
| 6,706,892 | B1 | 3/2004 | Ezrin et al. .................... 548/548 |
| 6,875,176 | B2 * | 4/2005 | Mourad et al. ................. 600/442 |
| 6,955,648 | B2 | 10/2005 | Mozayeni et al. ............. 600/454 |
| 7,233,819 | B2 * | 6/2007 | Eda et al. ....................... 600/411 |
| 7,309,315 | B2 * | 12/2007 | Kullok et al. .................. 600/558 |
| 2004/0002654 | A1 * | 1/2004 | Davidson et al. .............. 600/454 |
| 2004/0030268 | A1 | 2/2004 | Weng et al. ......................... 601/2 |
| 2005/0015009 | A1 * | 1/2005 | Mourad et al. ................. 600/438 |
| 2005/0065436 | A1 | 3/2005 | Ho et al. ........................ 600/431 |
| 2006/0079782 | A1 * | 4/2006 | Beach et al. ................... 600/450 |

OTHER PUBLICATIONS

Aaslid, Rune, Thomas-Marc Markwalder, and Helge Nornes. "Noninvasive transcranial Doppler ultrasound recording of flow velocity in basal cerebral arteries" J Neurosurg. 57:769-774, 1982.

Klingelhöfer, Jürgen, Dirk Sander, and Ingo Wittich. "Functional Ultrasonographic Imaging" In Babikian VL, Wechsler LR, eds. Transcranial Doppler Ultrasonography. Woburn, MA: Butterworth-Heinemann, 1999. pp. 49-66.

Campbell, J.K., J.M. Clark, D.N. White, and C.O. Jenkins. "Pulsatile Echo-encephalography" Acta Neurol Scand Suppl 45:1-57, 1970.

Dahl, Arve, David Russell, Rolf Nyberg-Hansen, Kjell Rootwelt, and Petter Mowinckel. "Simultaneous Assessment of Vasoreactivity Using Transcranial Doppler Ultrasound and Cerebral Blood Flow in Healthy Subjects" J. Cereb Blood Flow Metab 14(6):974-981, 1994.

Gao, L., K.J. Parker, R.M. Lerner, and S.F. Levinson. "Imaging of the Elastic Properties of Tissue—A Review" Ultrasound Med Biol 22(8):959-977, 1996.

Markwalder, Thomas-Marc, Peter Grolimund, Rolf W. Seiler, Fritz Roth, and Rune Aaslid. "Dependency of Blood Flow Velocity in the Middle Cerebral Artery on End-Tidal Carbon Dioxide Partial Pressure—A Transcranial Ultrasound Doppler Study" J. Cereb Blood Flow Metab 4(3):368-372, 1984.

* cited by examiner

FIG. 6B     FIG. 6C

ULTRASONIC TISSUE DISPLACEMENT/STRAIN IMAGING OF BRAIN FUNCTION

RELATED APPLICATIONS

This application is based on a prior provisional application, Ser. No. 60/915,897, filed on May 3, 2007, the benefit of the filing date of which is hereby claimed under 35 U.S.C. §119 (e).

GOVERNMENT RIGHTS

This invention was made with U.S. Government support under grant No. 1-R01-EB002198-01 awarded by the National Institute of Biomedical Imaging and Bioengineering. The U.S. Government has certain rights in the invention.

BACKGROUND

As early as the 1870s, it was observed that mental activity influences regional brain physiology. Several researchers demonstrated that the surface pulsations and the temperature of the brain increase with mental activity. The technology necessary to pursue this research was limited, and it was not until the 1950s that the first instrument for quantifying whole brain blood flow and metabolism in humans was developed. Though the mechanisms coupling neuronal activation and vascular response are not fully understood, it is generally accepted that neural activation triggers vasodilation of the supplying vessels, thereby increasing blood flow to activated areas in the brain.

Various modalities have been developed for functional brain imaging. Techniques such as electroencephalography (EEG) and magenetoencephalography (MEG) measure the electromagnetic fields produced during neuronal activation to map brain function. Other techniques such as functional near-infrared spectroscopy (fNIRS), functional magnetic resonance imaging (fMRI), positron emission tomography (PET), single photon emission computed tomography (SPECT), and functional transcranial Doppler sonography (fTCD) measure changes in blood flow or blood gas concentration as surrogates for detecting changes in neuronal activation.

The introduction of transcranial Doppler sonography (TCD) provided a non-invasive means to monitor blood flow through the major cerebral vessels in real-time using ultrasound. Functional TCD (fTCD) is the application of TCD for monitoring task-specific changes in cerebral blood flow. Early studies in fTCD focused on arterial velocity changes evoked through a simple light stimulation of the eye. Significant velocity changes were observed, particularly in the posterior cerebral artery (PCA), the principal vessel supplying the primary visual cortex. The range of studies has since expanded to include colored light, field-of-vision, half-field stimulation, intermittent stimulation, and stimulation with complex images. Changes in blood flow through the middle cerebral artery (MCA) associated with a specific stimulation have also been demonstrated. These studies focused on auditory stimulation, cognitive tasks, language, memory tests, and motor tasks. These studies were validated through direct comparison against the Wada test, which uses an anesthetic for lateral suspension of brain activity, and against fMRI, and established fTCD as a viable complementary tool for functional brain imaging. Functional TCD has since been applied to the study of migraines, stroke recovery, Alzheimer's disease, Parkinson's disease, Huntington's disease, and schizophrenia.

Compared to other brain imaging systems such as PET, SPECT, and MRI, TCD is a rapid, portable, inexpensive, continuous monitoring technique that can be applied to subjects and in settings unsuitable for study by other neuroimaging techniques. Functional TCD is limited, however, in its ability to localize regions of activity; TCD can only be used to measure flow through larger segments of the cerebral vasculature that supply blood to large regions of the brain spanning multiple functional areas because the signal backscattered by blood is significantly less than that backscattered by tissue. In addition, the skull significantly attenuates ultrasound; researchers have reported the attenuation of the skull to be 13 dB/cm/MHz. Therefore, to measure blood flow, TCD is generally limited to application through the three "acoustic windows," including the temporal bone window, the orbital window, and the foramen magnum window. Use of only these three windows for this purpose limits the regional access available with fTCD. Furthermore, 5-8% of the population do not have any adequate acoustic window for applying TCD.

Thus, it would be desirable to provide more robust and less limited techniques for imaging brain functions.

SUMMARY

Disclosed herein is an ultrasound based method for rapid, portable, functional brain imaging. The technique, referred to as Tissue Pulsatility Imaging (TPI), infers function from ultrasonically measured displacement and/or strain of brain tissue due to the natural, local, pulsatile change in blood volume over the cardiac and respiratory cycles. This technique differs from previous functional ultrasonic imaging methods by: (1) measuring tissue motion as a surrogate for blood, flow rather than measuring blood flow itself, and, (2) enabling ultrasound images to be obtained directly through the skull from almost any location, rather than just through an anatomical window (such as the temporal bone window), which is possible because tissue backscatters significantly more ultrasound than blood. One advantage of TPI is that it combines/offers the imaging capability of larger and more expensive systems, such as Magnetic Resonance Imaging (MRI) and PET systems, while maintaining the ease of use and portability that are characteristics of fEEG and near infrared spectroscopy (NIRS).

Significantly, by measuring tissue motion and/or tissue strain (the derivative of motion with depth) rather than blood velocity, TPI is able to overcome the limitation of low backscatter from blood that limits ultrasound access to the brain via the skull's acoustic windows. This technique has been empirically validated by measuring the hemodynamic response associated with visual stimulation of the occipital cortex using a contrast-reversing checkerboard paradigm.

TPI is based on characterizing blood flow and perfusion by measuring the natural tissue expansion and relaxation over the cardiac and respiratory cycles. During systole, blood enters tissue through the arterial vasculature faster than it leaves through the venous vasculature, causing blood to accumulate and the tissue to expand or swell by a fraction of a percent. During diastole, venous drainage dominates, allowing the tissue to return to its pre-systolic volume. The rate of venous drainage is modulated by the respiratory cycle, if the tissue is not elevated above the chest, which results in a periodic expansion of nearly one percent synchronized with respiration, in addition to the cardiac pulsatile expansion.

TPI is somewhat related to a much older, established technique referred to as plethysmography, which has been a popular noninvasive diagnostic method for the assessment of arterial and venous disease since the 1960's. Plethysmography works by measuring whole limb expansion due to vascular perfusion in association with the cardiac cycle (arterial) or the respiratory cycle (venous). With TPI, ultrasound is used to measure tissue displacement or strain to provide the plethysmographic like signal from hundreds or thousands of small volumes of tissue within an ultrasound image plane in only a portion of a limb or body part, rather than the gross plethysmographic signal from an entire limb or body part, as is done with traditional plethysmography. Significantly, TPI enables displacement/strain levels from many different parts of the brain to be compared with each other, in order to determine which portions of the brain exhibit increased displacement/strain in response to visual or other stimuli.

To summarize, functional TPI maps brain function by measuring changes in tissue pulsatility due to changes in blood flow with neuronal activation. TPI uses tissue Doppler signal processing methods to measure a pulsatile "plethysmographic" signal from hundreds or thousands of sample volumes in an ultrasound image plane. A feasibility study conducted to determine if TPI could be used to detect regional brain activation during a visual contrast-reversing checkerboard block paradigm stimulus showed that in 7 out of 14 tests, consistent regions of activation were detected from tissue around the major vessels perfusing the visual cortex. During each test, ultrasound data were collected transcranially from the occipital lobe as a subject viewed alternating blocks of a reversing checkerboard (stimulus condition) and a static, gray screen (control condition). Multivariate Analysis of Variance (MANOVA) was used to identify sample volumes with significantly different pulsatility waveforms during the control and stimulus blocks.

In the empirical study, displacement was measured voxel-by-voxel throughout the image sector using a standard two-dimensional (2-D) Doppler autocorrelation estimator. After high pass filtering to substantially reduce the effect of respiratory motion, the peak to peak displacement for each voxel over each cardiac cycle was measured as a metric of pulsatility. A paired t-test was used to identify voxels with significantly different ($p<0.01$) pulsatilities during the control and stimulation blocks. The results from the empirical study indicate that there is a potential role for ultrasound in regional functional brain imaging, and that a functional ultrasonic imaging system could provide value in emergency medicine and in the management of brain injury.

Yet another aspect of the concepts disclosed herein is the use of TPI to monitor cerebral vasoreactivity (reduced cerebral vasoreactivity is associated with many medical conditions, and a procedure for monitoring cerebral vasoreactivity is thus a useful diagnostic tool).

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein:

FIG. 1A graphically illustrates a conventional (Prior Art) gross plethysmographic signal;

Figure 3A:
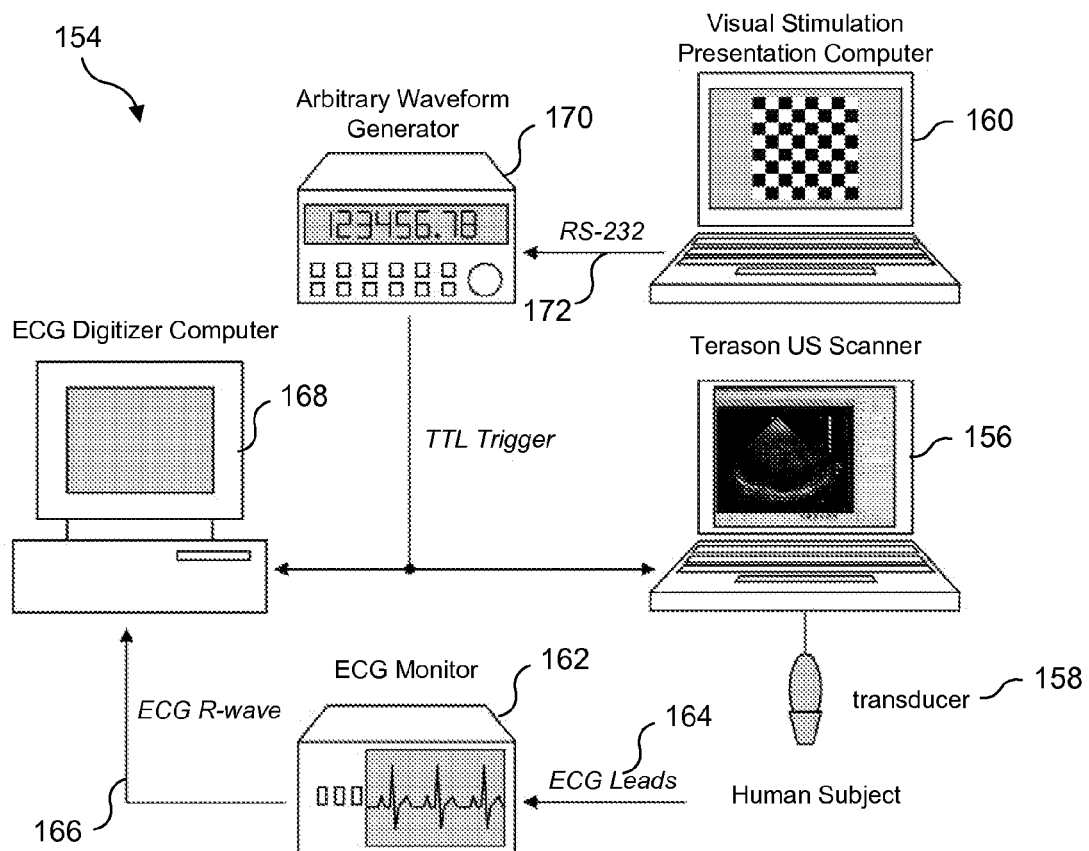
FIG. 3A is a functional diagram of an empirical data acquisition system for brain function mapping studies using TPI.
Figure 3B:
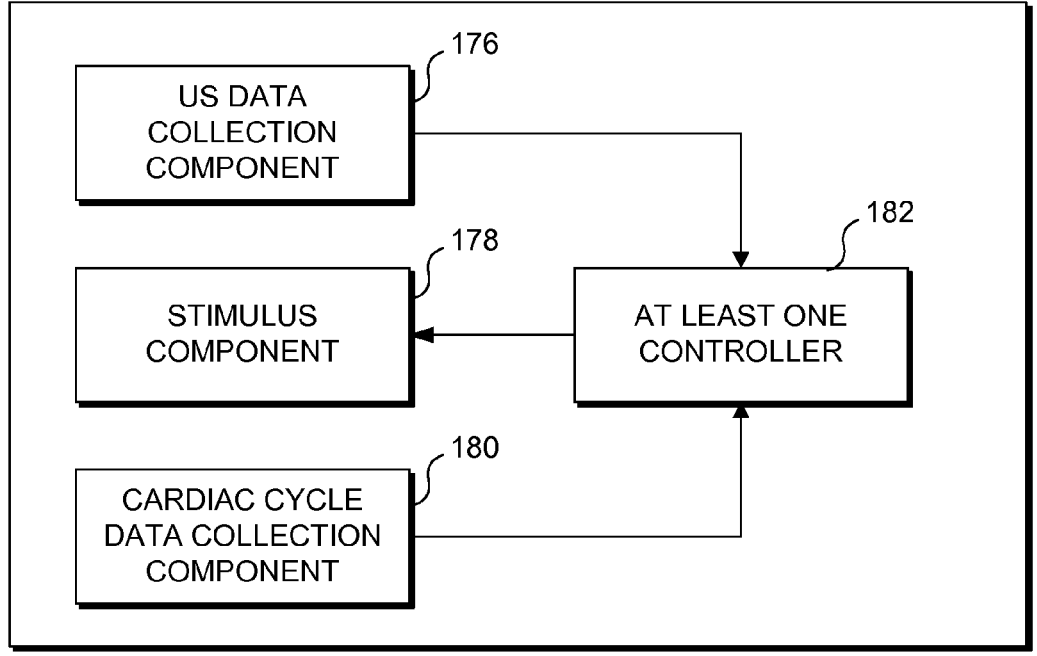
FIG. 3B is a functional diagram of a simplified exemplary data acquisition system for brain function mapping studies using TPI.
Figure 4:
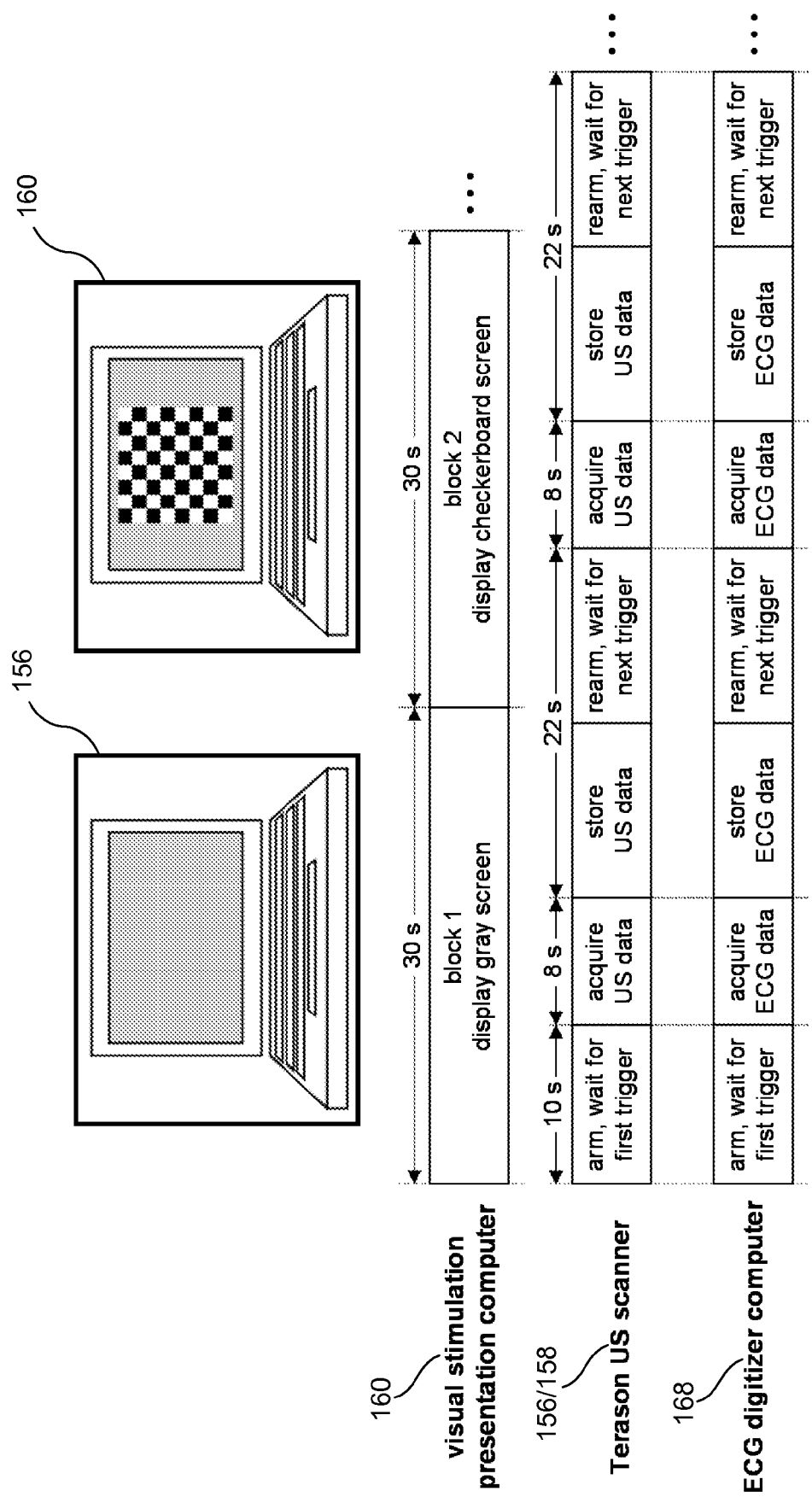
Figure 5:
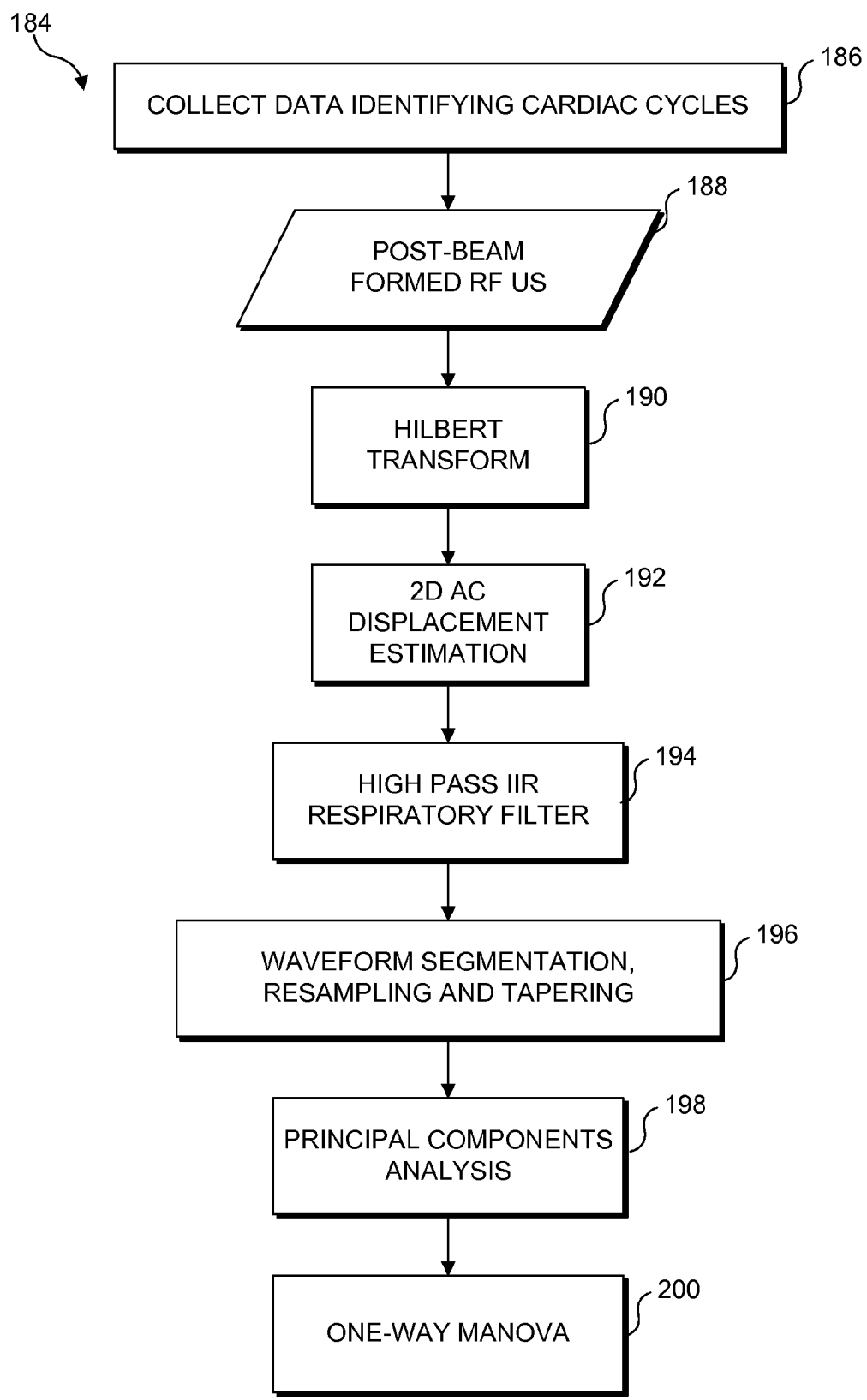
Figure 6A:
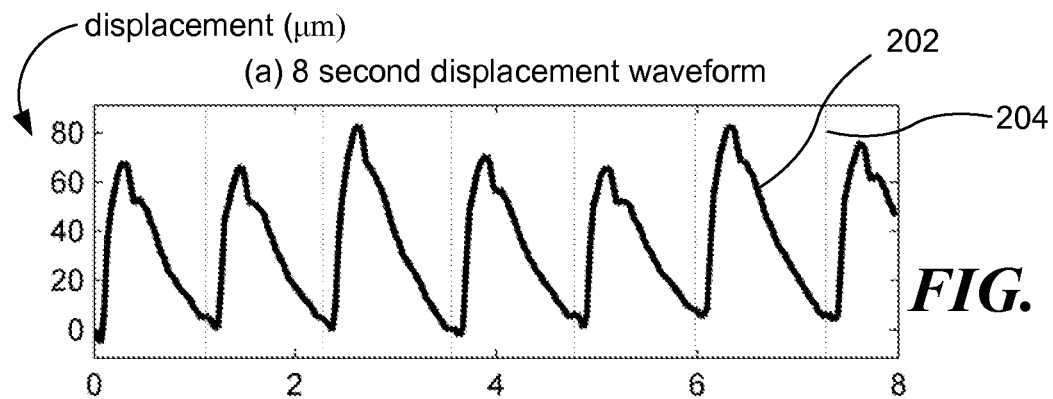
Figure 7A:
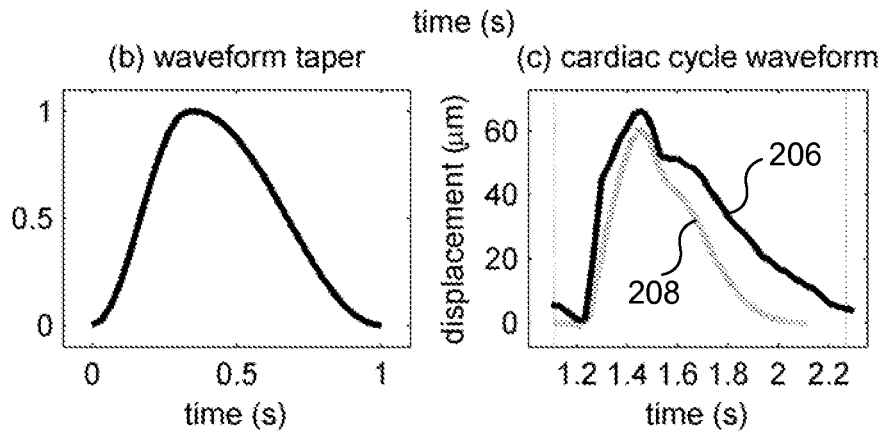
Figure 7A:
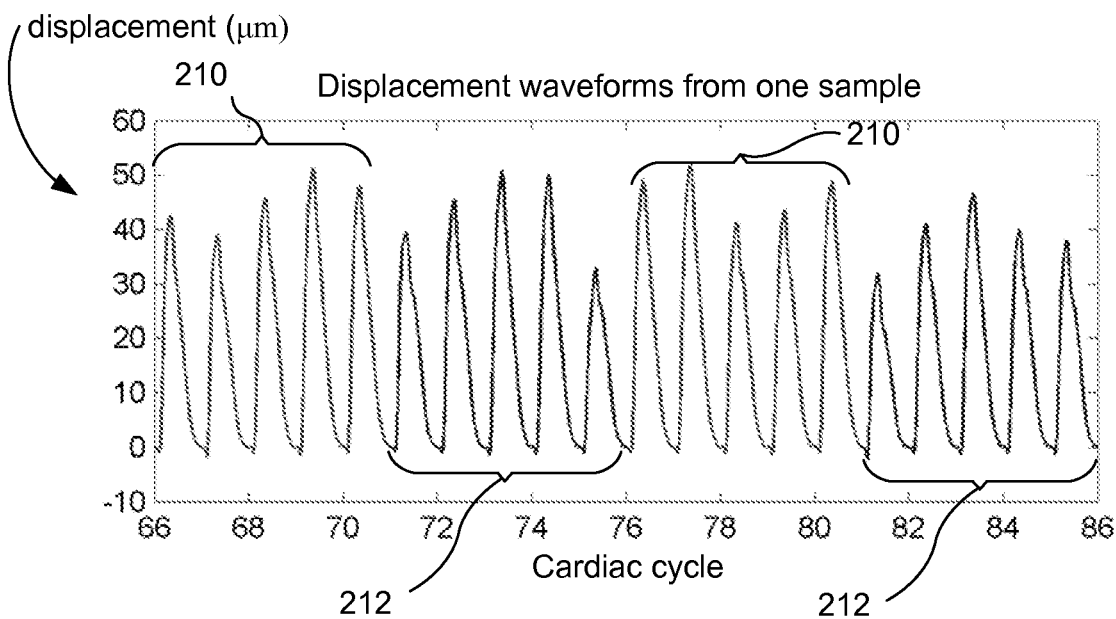
Figure 7B:
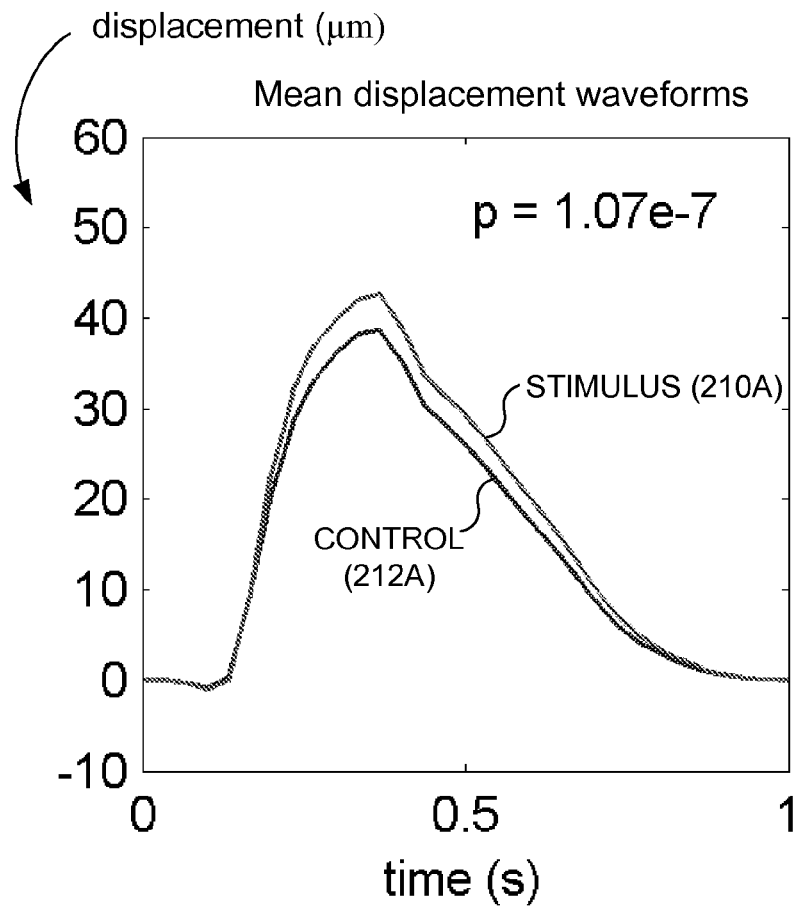
Figure 9:
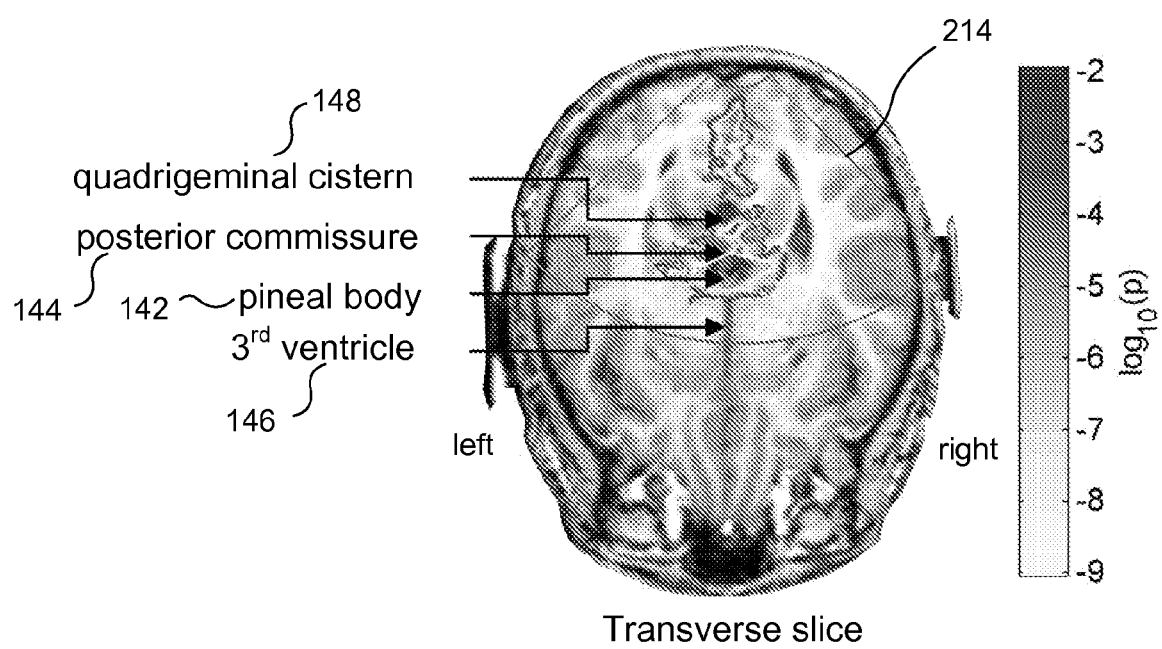
Figure 8:
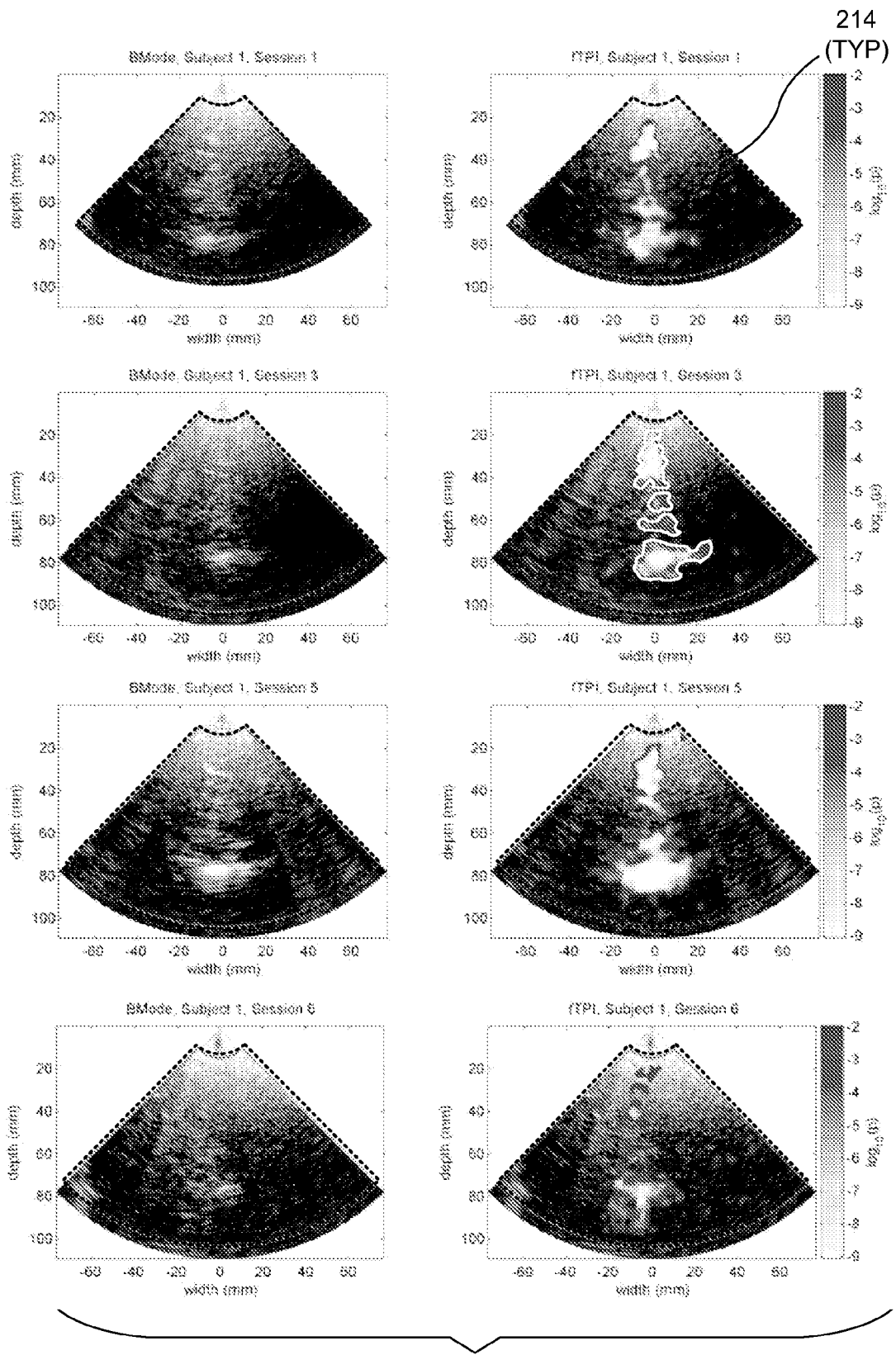
Figure 10A:
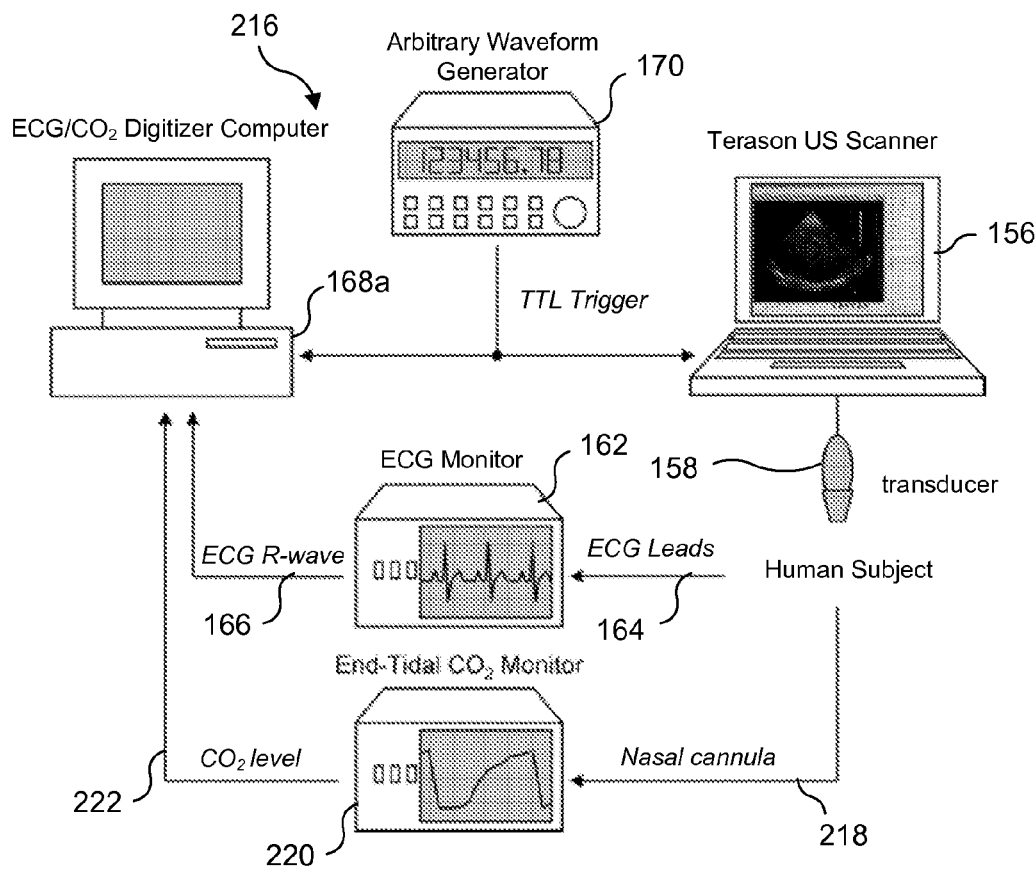
Figure 10B:
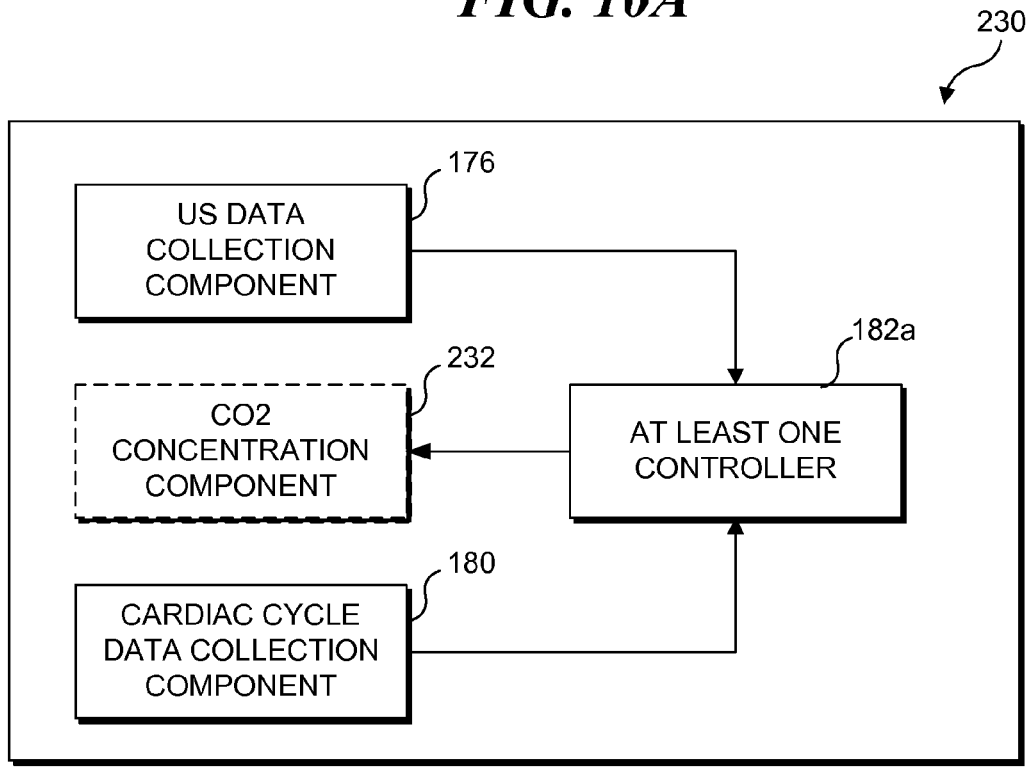
Figure 11:
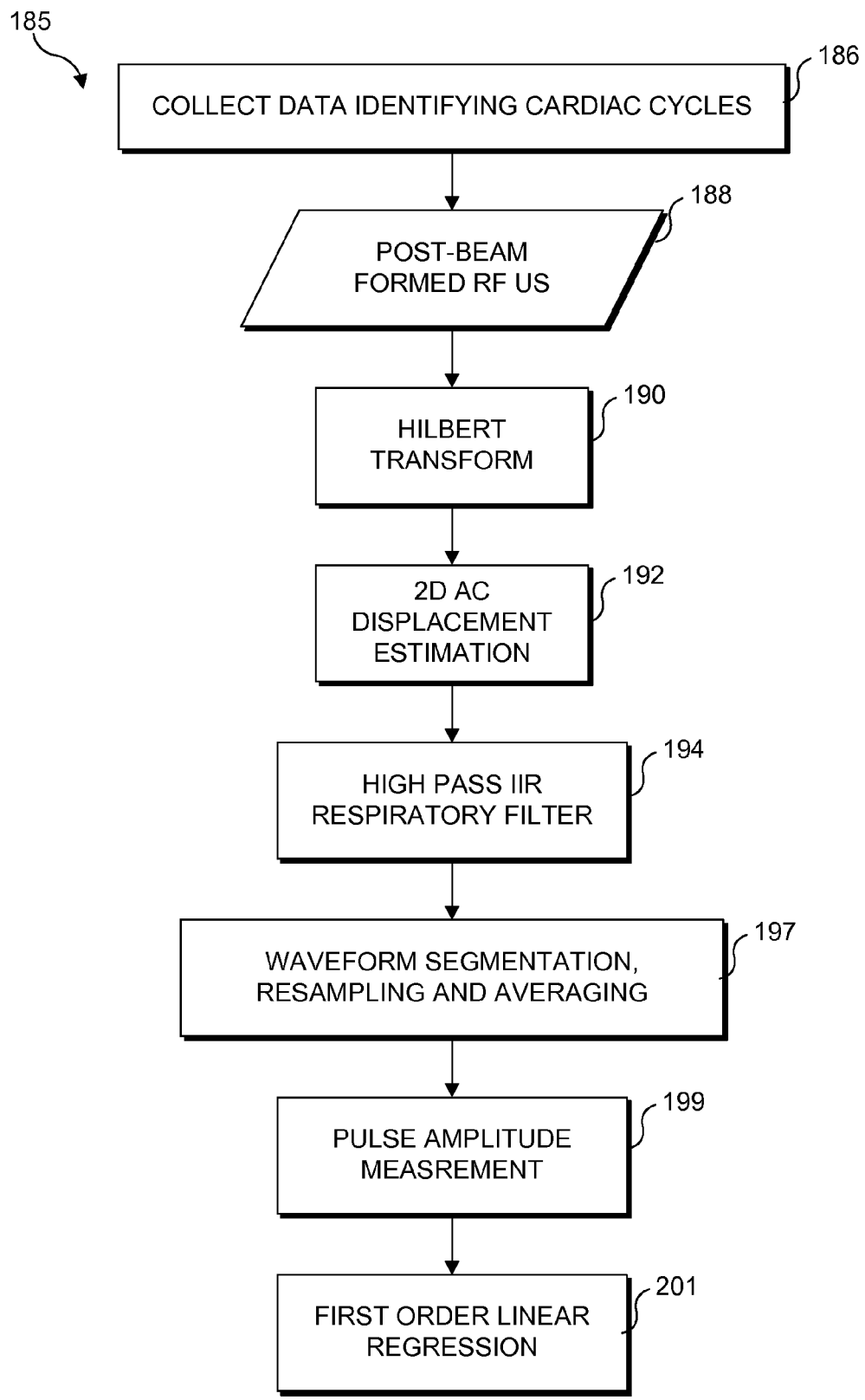
Figure 12A:
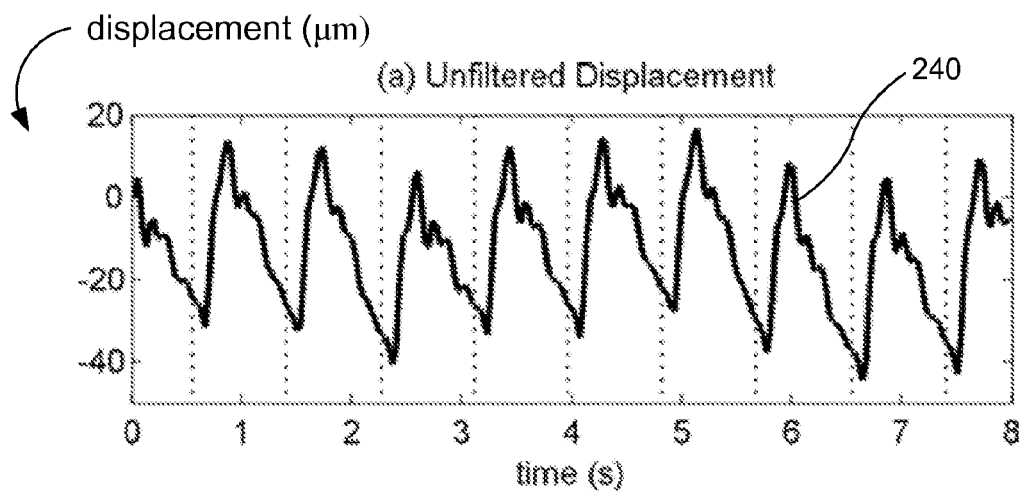
Figure 12B:
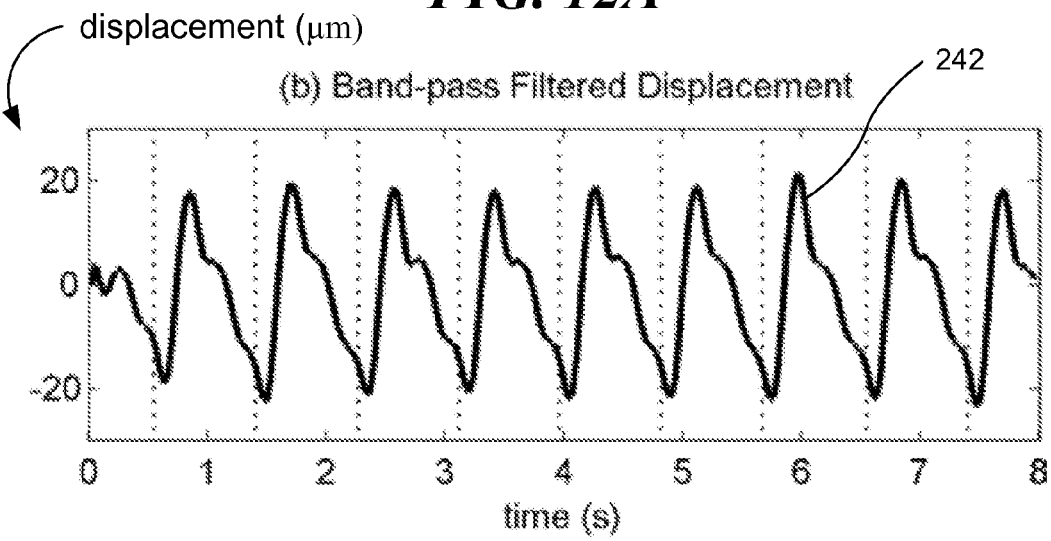
Figure 12C:
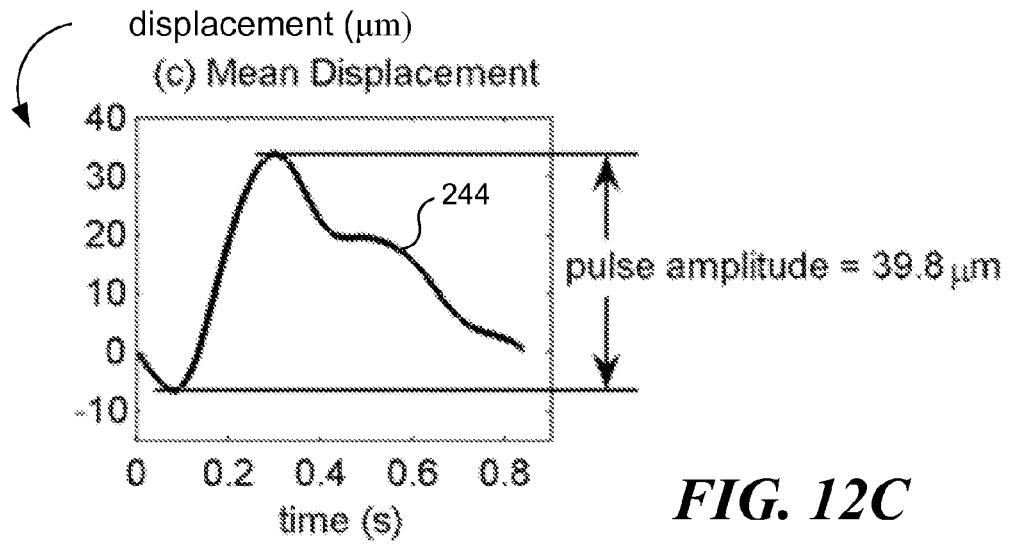
Figure 13A:
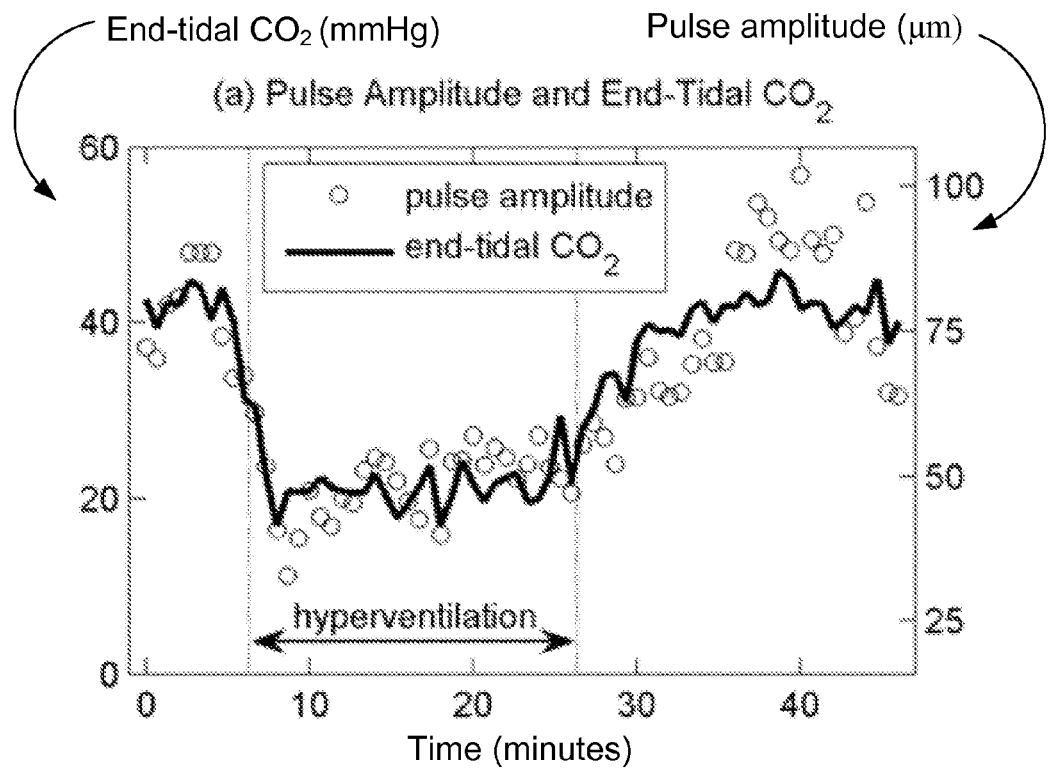
Figure 13B:
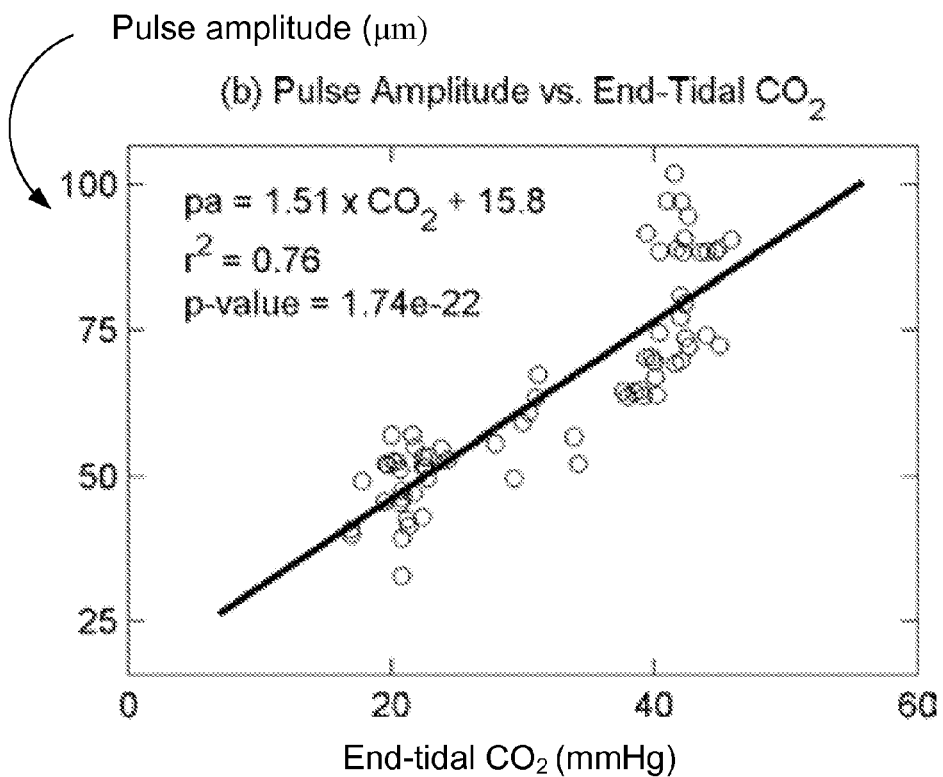
Figure 14A:
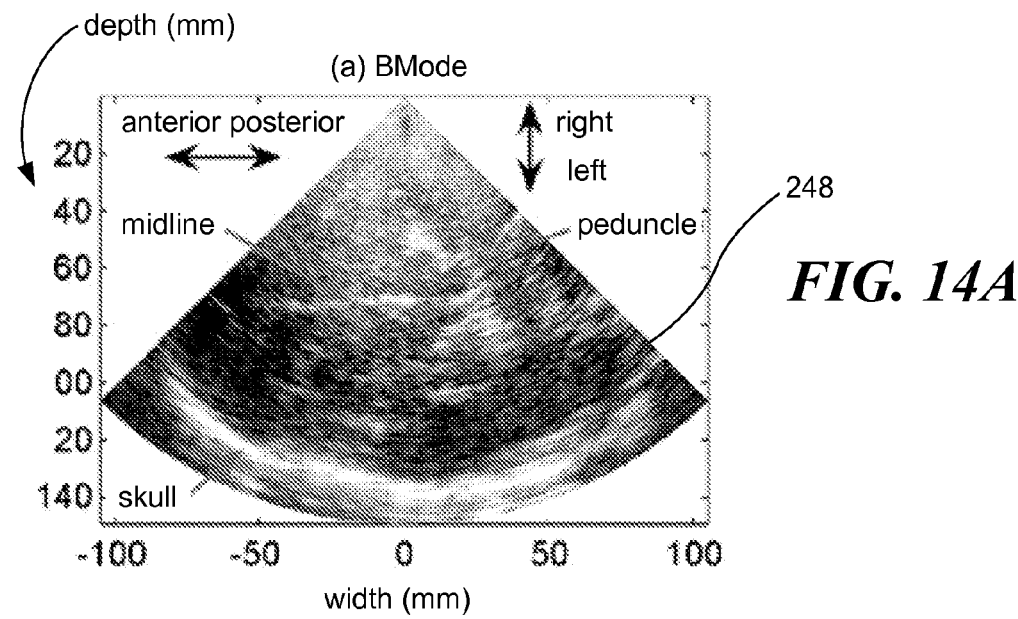
Figure 14B:
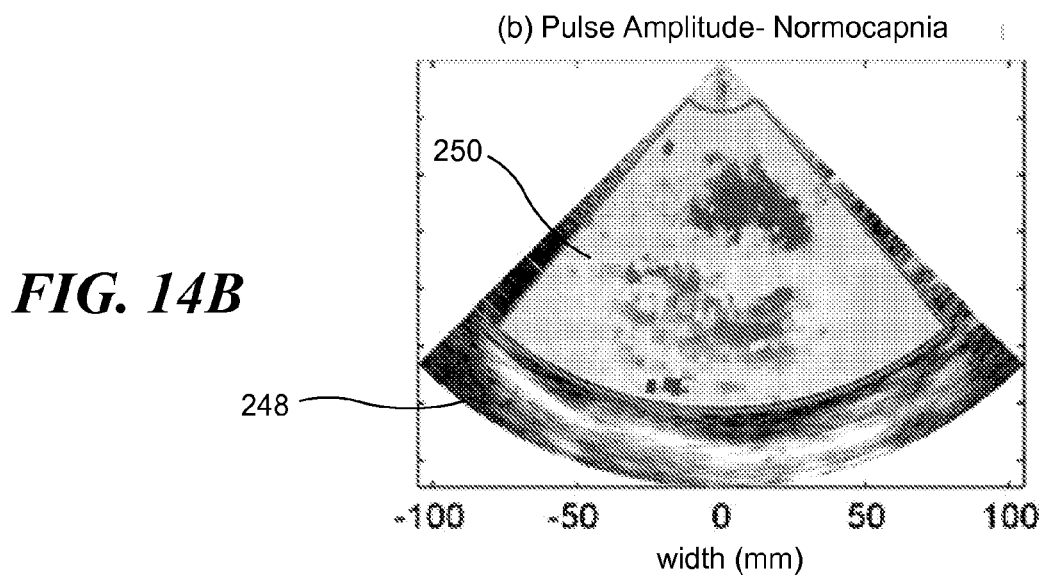
Figure 14C:
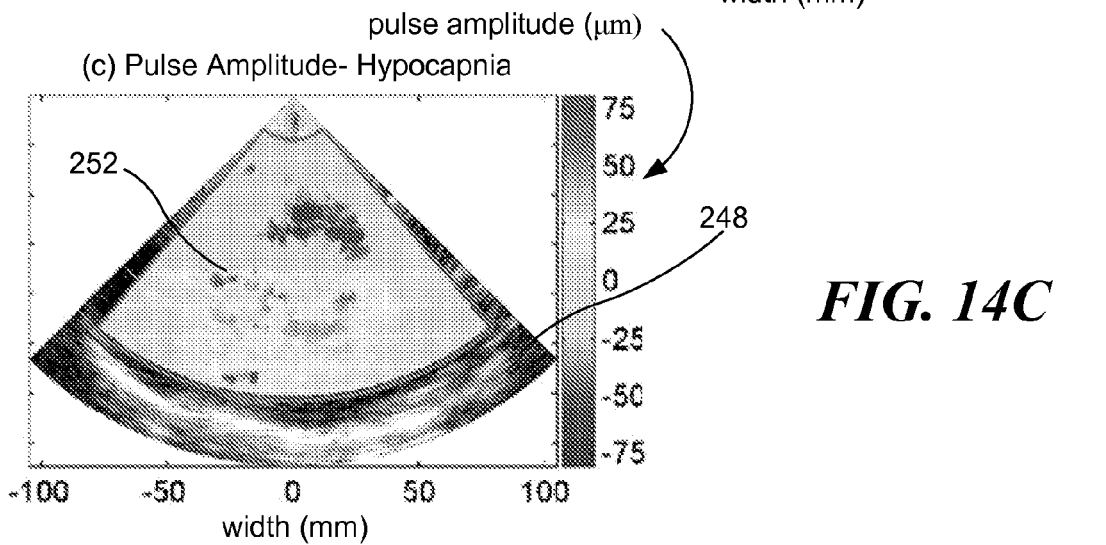
Figure 15:
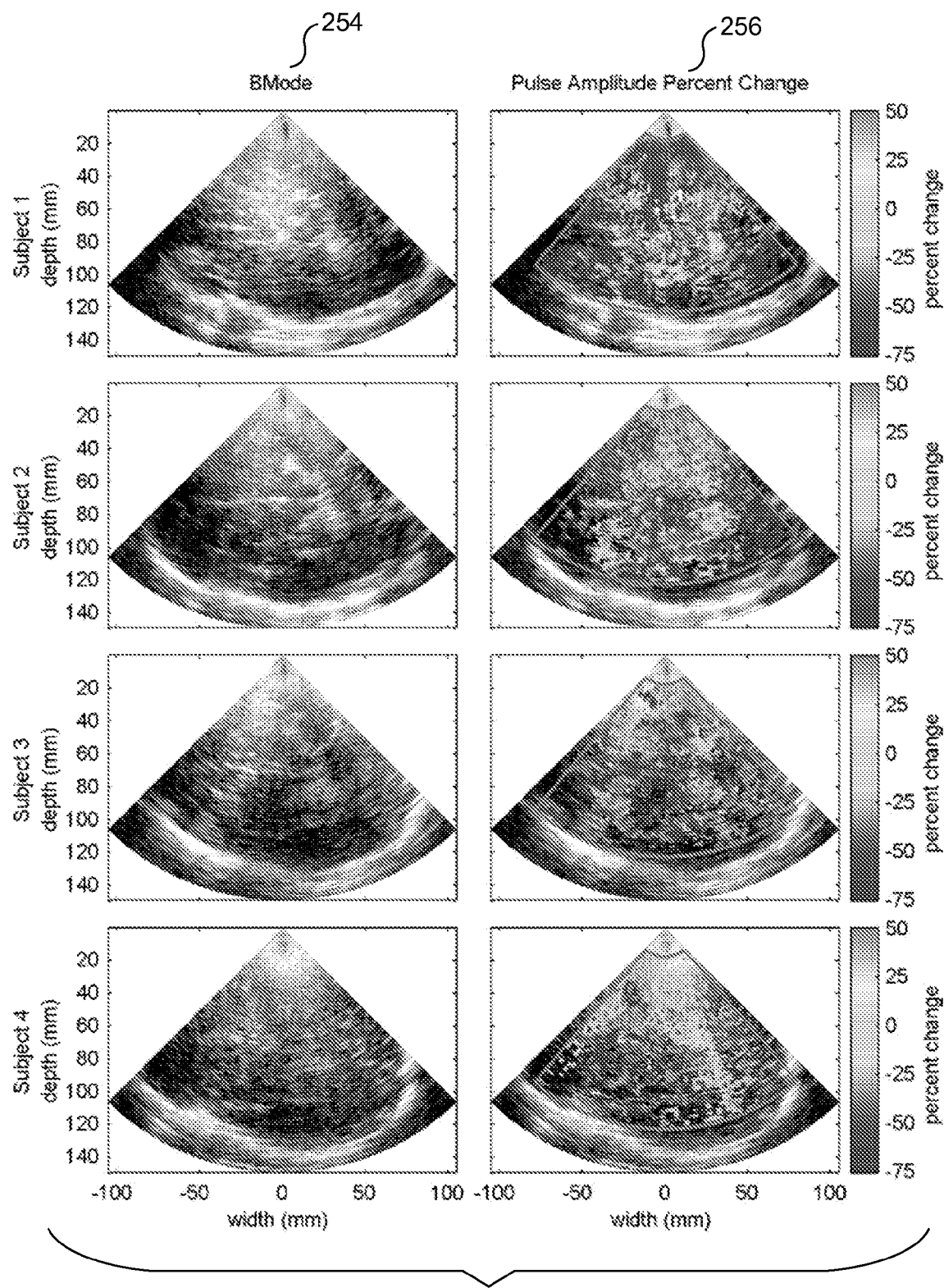
Figure 16A:
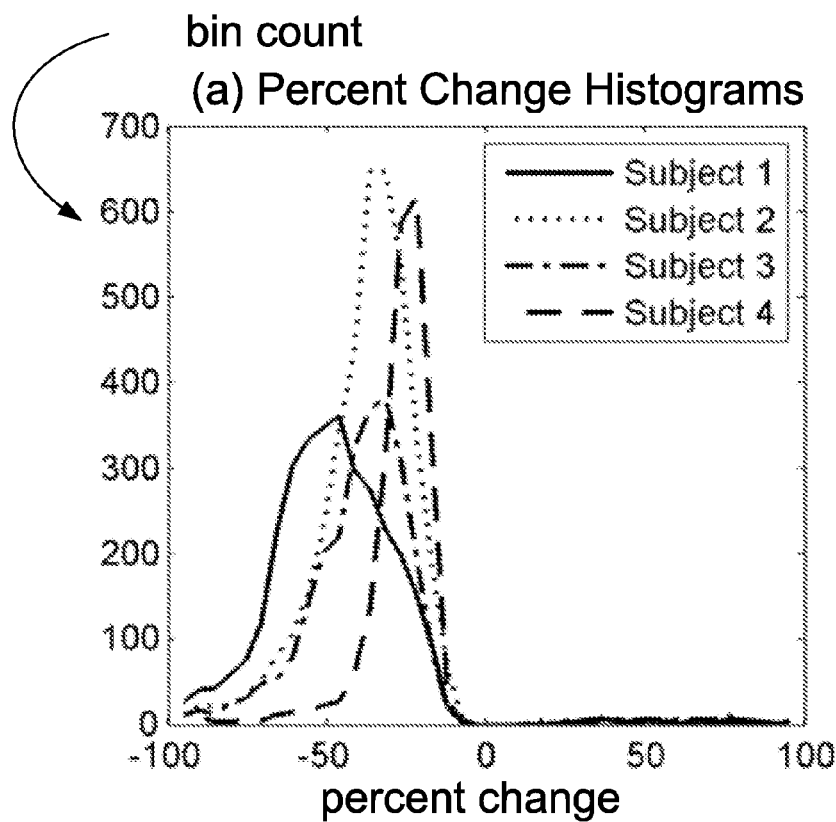
Figure 16B:
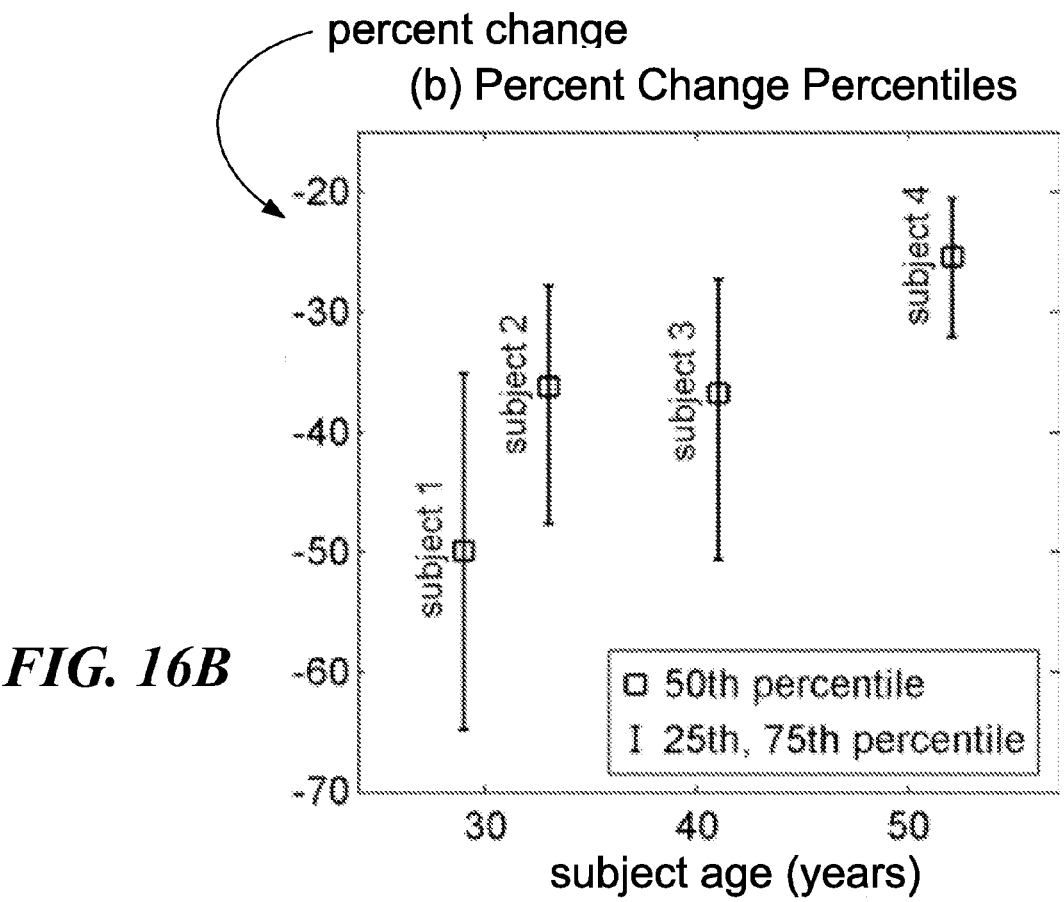

FIG. 4 schematically illustrates an exemplary synchronization technique implemented by the system of FIG. 3, to synchronize the application of visual stimulation and data acquisition;

FIG. 5 is an exemplary flowchart illustrating the basic steps employed in using TPI to map brain function;

FIG. 6A represent an exemplary 8 second displacement waveform during a control block for a sample volume near the brain stem after filtering to substantially reduce the effect of respiratory motion;

FIG. 6B graphically represents a modified 31-sample Hann window;

FIG. 6C graphically represent one cardiac cycle (as indicated by the solid line) from FIG. 6A and the waveform after tapering (as indicated by the dotted line);

FIG. 7A graphically illustrates displacement waveforms for two control blocks and two checkerboard blocks for one sample volume;

FIG. 7B graphically illustrates mean waveforms from all the cardiac cycles for the control blocks and all of the checkerboard blocks for the sample volume;

FIG. 8 is a composite image including B-mode images (left column) and functional TPI data (right column) collected from a male test subject, showing consistency among the results from four different TPI studies of the male subject;

FIG. 9 schematically illustrates exemplary p-values for one of the sessions superimposed on an MRI image slice approximately corresponding to the ultrasound image plane employed to collect the TPI data;

FIG. 10A is a functional diagram of an empirical data acquisition system for monitoring cerebral vasoreactivity using TPI;

FIG. 10B is a functional diagram of a simplified exemplary data acquisition system for monitoring cerebral vasoreactivity using TPI;

FIG. 11 is an exemplary flowchart illustrating the basic steps employed in using TPI to monitor cerebral vasoreactivity;

FIG. 12A graphically illustrates a displacement waveform from one dataset from a single sample volume from subject 4, before band-pass filtering;

FIG. 12B graphically illustrates the displacement waveform of FIG. 12A after the band-pass filtering;

FIG. 12C graphically illustrates a mean displacement waveform calculated by averaging cardiac cycles from the waveform of FIG. 12B;

FIG. 13A graphically illustrates end-tidal $CO_2$ from subject 3, along with pulse amplitude measurements from a single sample volume;

FIG. 13B graphically illustrates pulse amplitude versus end-tidal $CO_2$ from the same sample volume along with the best-fit line with first-order linear regression;

FIG. 14A is a transverse B-mode image of the brain and skull of subject 2;

FIG. 14B is a pulse amplitude image of the brain of subject 2 at rest (i.e., before hyperventilation) with an end-tidal $CO_2$ of 41.7 mm of Hg;

FIG. 14C is a pulse amplitude image of the brain of subject 2 during hyperventilation with an end-tidal $CO_2$ of 20.7 mm of Hg;

FIG. 15 includes B-mode images from all of the subjects along with the predicted percent change in pulse amplitude for a change in end-tidal $CO_2$ from 40 mm Hg to 20 mm Hg, for samples volumes with linear regression p-values less than 0.01;

FIG. 16A graphically illustrates histograms of percent changes from the four subjects for sample volumes with linear regression p-values less that 0.01; and FIG. 16B graphically illustrates the median, $25^{th}$ and $75^{th}$ percentiles for percent changes for p-values less than 0.01 arranged by subject age.

DESCRIPTION

Figures and Disclosed Embodiments Are Not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein.

As used herein, Tissue Pulsatility Imaging (TPI) is an extension of tissue Doppler imaging methods for measuring and characterizing the natural, pulsatile expansion and relaxation of tissue over the cardiac cycle as an indirect measurement of perfusion. Functional Tissue Pulsatility Imaging (fTPI) is an application of TPI for mapping brain function based on the change in tissue pulsatility with regional activation.

Figure 1A:
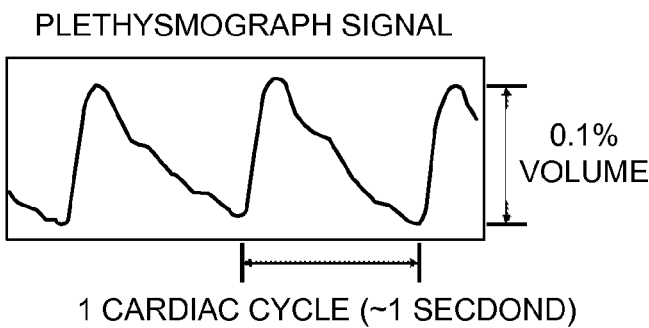
FIG. 1B is a flowchart illustrating the basic steps employed in TPI.

TPI is a novel extension of plethysmography, which has been used for nearly 100 years to measure the gross change in tissue volume in the arms, legs, fingers, toes and other isolatable whole body parts. Tissue volume changes cyclically with the cardiac cycle as blood accumulates in and drains from the arterial vasculature. FIG. 1A graphically illustrates a conventional (Prior Art) gross plethysmographic signal. Whereas conventional plethysmography is a single gross plethysmographic measurement of tissue volume change, TPI uses pulsed Doppler ultrasound to measure local "plethysmographic" signals from 100s or 1000s of sample volumes throughout the ultrasound image plane.

With respect to the motion of brain tissue, note that the brain volume constrained by skull. Expansion of brain tissue compresses ventricles. With each cardiac cycle, the brain initially moves medially, posteriorly, and caudally. As described in detail below, empirical studies have indicated that TPI can measure the motion of brain tissue with a resolution of approximately one micron. By measuring tissue motion rather than blood flow, ultrasound can be used to indirectly measure changes in blood flow in the brain from locations other than through the traditional acoustic windows in the skull. In addition to using TPI for mapping brain function, empirical data indicate that TPI can be used to monitor cerebral vasoreactivity, which is a commonly employed diagnostic indicator.

When a portion of the brain responds to stimulus, changes in blood flow occur at that portion of the brain. The change in blood flow in turn induces a change in the motion of the brain tissue. Brain tissue naturally moves (or pulsates) due to the respiratory cycle and the cardiac cycle. TPI is based on distinguishing motion of brain tissue that is different from the motion due to the cardiac cycle and the respiratory cycle.

Figure 1B:
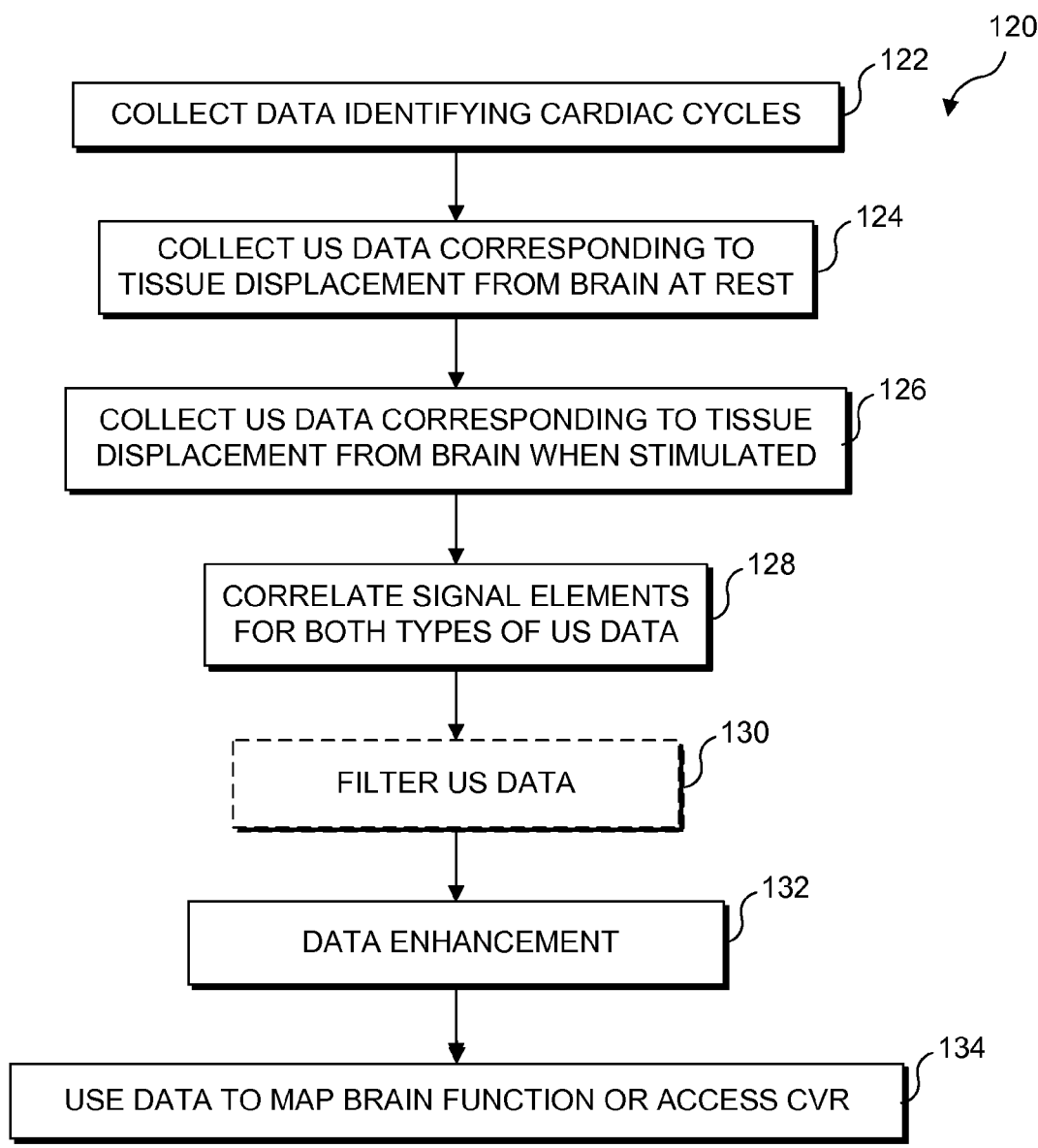

FIG. 1B is a flowchart 120 illustrating the basic steps employed in TPI, to overcome the limitation of low backscatter from blood that limits ultrasound access to the brain via the skull's acoustic windows. As described in greater detail below, TPI measures tissue displacement (or tissue strain) in the brain, and this displacement data (or strain data) can be used to map brain function and to monitor cerebral vasoreactivity.

In a block 122 cardiac cycles are identified. An exemplary technique for tracking cardiac cycles is to use electrocardiogram (ECG) data. With each cardiac cycle, blood flows into the brain and causes the brain to expand. TPI measures this expansion (or the displacement of the tissue) as a surrogate for measuring blood flow. Note there may be additional components in the TPI signal beyond motion due to cardiac cycles, such as motion due to respiration (which can be separated from cardiac motion and used for monitoring CVR), and motion due to blood flow associated with neural stimulation (which can be separated from cardiac motion and used for mapping brain function). Collecting an ECG signal from the subject undergoing TPI enables the beginning of each cardiac cycle to be identified, so that tissue motion from multiple cardiac cycles can be averaged. Thus, the ECG data are used to isolate and process the displacement/strain signals over multiple cardiac cycles. Strictly speaking, the ECG data are not essential, in the present novel approach, because the beginning of each cardiac cycle can be identified using other techniques, such as from a blood pressure waveform measured elsewhere in the body (e.g., an arm) or derived from some other source, but ECG data are relatively easy to acquire, as described above, and this approach is quite accurate.

In a block 124 ultrasound data are collected to measure tissue displacement in the brain when the subject is quiescent (i.e., the subject has not been exposed to physical or mental stimulation). The specific portion of the brain being imaged will be a function of the desired goal (i.e., brain function mapping or monitoring cerebral vasoreactivity). In a block 126, ultrasound data are collected to measure tissue displacement in the brain when the subject has been stimulated (mental stimulation for brain function mapping, and hyperventilation for monitoring cerebral vasoreactivity). It should be recognized that many different types of transducers can be used to provide the ultrasound data. While 2-D ultrasound represents an exemplary type of ultrasound, it should be recognized that the concepts disclosed herein are not limited to the use of 2D ultrasound data.

In a block 128 the raw ultrasound data for both data sets (i.e., while the patient is stimulated and at rest or quiescent) are processed to correlate signal elements. Those of ordinary skill in the arts will recognize that the correlation process is a function of the type of transducer used to collect the ultrasound data. Common correlation techniques include cross correlation and autocorrelation. In at least some exemplary embodiments, the initial signal processing (i.e., processing of the data in block 128) includes a transform operation (as discussed in greater detail below).

In an optional block 130, the correlated ultrasound data are filtered. The specific type of filtering will be a function of the type of TPI analysis (i.e., brain function mapping, or monitoring cerebral vasoreactivity) that is being performed. Beneficial filtering techniques include, but are not limited to, filtering to remove (or at least substantially reduce) displacement data corresponding to respiratory motion, and possibly filtering to remove (or at least substantially reduce) displacement data corresponding to cardiac motion. The empirical studies discussed below employed a high pass filter to separate cardiac signal elements from respiratory signal elements, to focus the analysis on the cardiac signal portion. A low pass filter could be employed to focus the analysis on the respiratory signal portion.

It should be noted that other motion sources may be identified and removed via filtering. For example, in one embodiment, the ECG data (or other types of data) can be used to detect abnormal heart beats, so that they can be excluded from the analysis. Thus, the filtering techniques noted above are intended to be exemplary, rather than limiting, and other types of filtering to remove motion arising from various specific undesired sources can be implemented.

In block 132 data enhancements are performed. A particularly significant data enhancement is re-sampling, in which the ultrasound displacement data are re-ordered such that the first ultrasound pulse in a data sample coincides with the beginning of the cardiac cycle, as determined in block 122. This step eliminates the need for the ultrasound data acquisition to be synchronized with the cardiac cycle. If desired, the cardiac cycle data collected in block 122 can be used to control ultrasound acquisition, such that re-sampling is not required. As discussed in greater detail below, additional enhancements include waveform segmentation and waveform tapering.

In at least one embodiment (i.e., using TPI to map brain function), the processed ultrasound data for brain tissue displacements when the patient is at rest and when stimulated are compared to identify tissue displacements associated with stimulation. Exemplary (but not limiting) processing steps are described in greater detail below with respect to empirical studies conducted to study the use of TPI for brain function mapping and monitoring cerebral vasoreactivity. In a block 134, the ultrasound data are used to either map brain function, or to monitor cerebral vasoreactivity.

Conceptually, it should be noted that the initial data acquisition steps can be considered to correspond to measuring small changes in displacement, while the latter analysis steps can be considered to correspond to measuring small differences in displacement. Furthermore, it should be recognized that at least with respect to using TPI for mapping brain function, empirical studies indicate that tissue strain (the derivative of motion with depth) can be employed as well as tissue displacement.

The following sections describe details of empirical studies using TPI to map brain function and to monitor cerebral vasoreactivity.

The Use of TPI to Map Brain Function: Subjects: Two subjects participated in the empirical study, a 34 year-old, right-handed male and a 39 year-old, left-handed female. Both subjects had normal, uncorrected vision. A total of seven sessions were conducted on each subject over a four week period. For each session, the two subjects were studied on the same day, approximately 30 minutes apart. No effort was made to control the day of the week, the time of day, or caffeine intake at which the sessions occurred. Written informed consent was obtained from both subjects. The research protocol was approved by the Human Subjects Committee of the University of Washington. Full three-dimensional (3-D) anatomical and angiographic MRI data were collected for the male subject as part of another approved study and were used to identify the location of the occipital lobe and other structures in the brain of this subject.

Protocol: During a session, the subject lay prone on a massage table with his/her head securely and comfortably positioned within the table's face donut. ECG leads were attached to the subject's arms, and ultrasound gel was applied to the back of the subject's head. A Terason 4V2™ phased-array transducer (Teratech Corp., Burlington, Mass.) held by an articulated clamp (Manfrotto, Bassano del Grappa, Italy) securely mounted to a laboratory bench was positioned at the back of the head of the subject, over the visual cortex and approximately 2 cm superior to the occipital protuberance and 0 to 2 cm lateral from the midline. Before locking the clamp in position, the transducer was oriented by an experienced sonographer to image a nearly transverse plane passing through the pineal body, which is hyperechoic in most individuals due to calcification. The visual stimuli were displayed on a computer monitor (a Dell Corporation, model Latitude D610™) approximately 75 cm directly below the subject's face. Prior to the start of the study, the lights were dimmed and a visual shield was placed around the front of the table to minimize visual distractions.

Figure 2A:
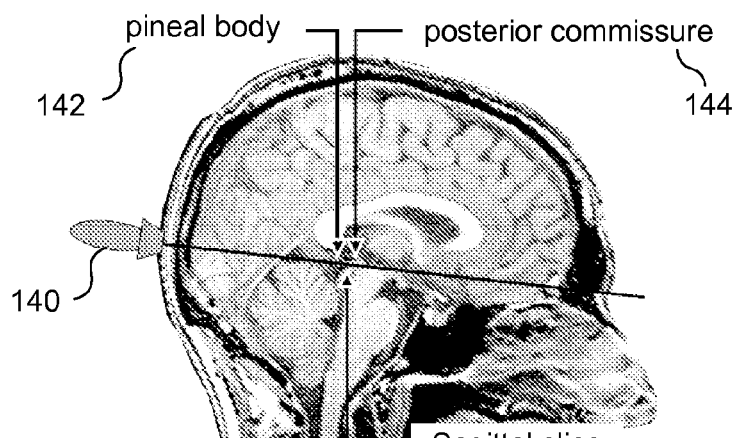
FIGS. 2A and 2B illustrate exemplary positioning of the ultrasound probe during brain function mapping studies using TPI.
Figure 2B:
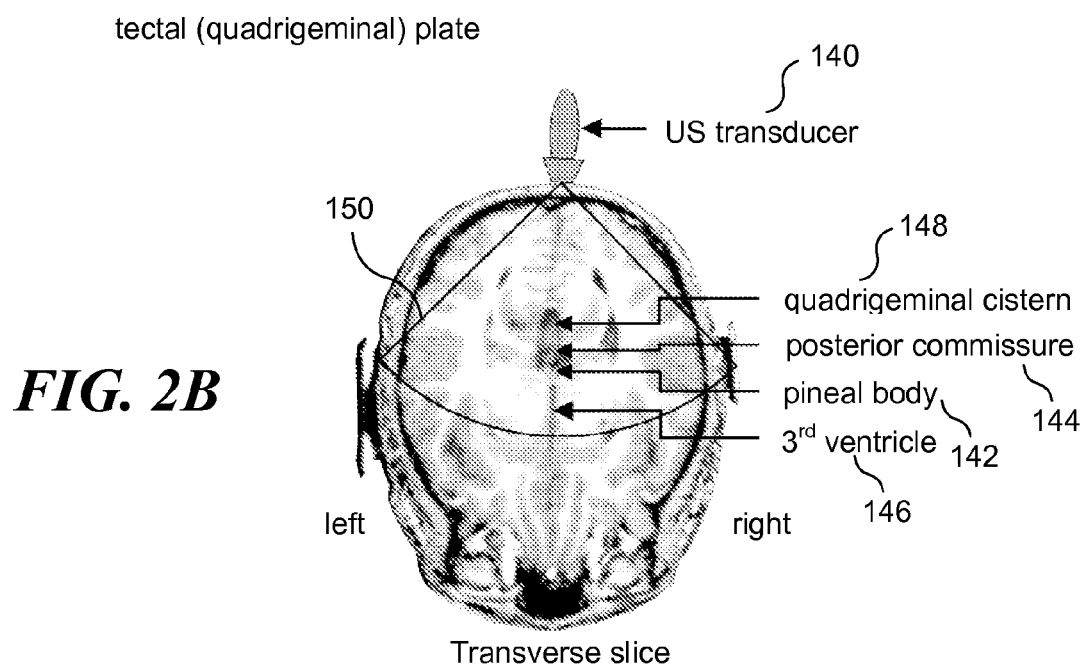
Figure 2C:
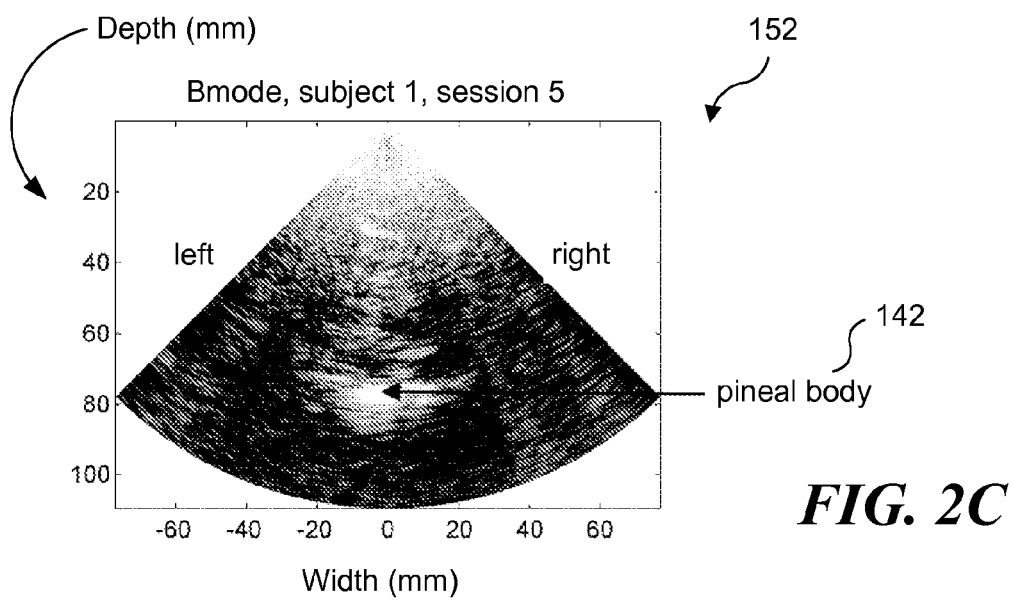
FIG. 2C is an exemplary B-mode image acquired using probe positioning as indicated in FIGS. 2A and 2B.

FIGS. 2A and 2B illustrate exemplary positioning of an ultrasound probe 140 during brain function mapping studies, while FIG. 2C is an exemplary B-mode image 152 acquired using such positioning. Note that FIGS. 2A and 2B are based on actual MRI images. The following structures are identified in one or more of FIGS. 2A and 2B: a pineal body 142, a posterior commissure 144, a quadrigeminal cistern 148, and a $3^{rd}$ ventricle 146. A black sector 150 in FIG. 2B generally corresponds to the location and extent of exemplary B-mode image 152 (FIG. 2C). It must be recognized that the empirical study was limited to tracking visual brain stimulation. Thus, the ultrasound probes are positioned to image the visual cortex. If other types of mental stimulation (such as motion, sound, taste, smell, or touch) were being provided, then the probe would be positioned accordingly. Furthermore, a commercial system will likely include a plurality of ultrasound probes distributed at different locations around the skull, to enable displacement/strain data to be collected from many different parts of the brain at the same time. The limiting factor in the number of ultrasound probes used is likely to be cost (i.e., from a data collection standpoint, it is likely better to have more probes than fewer probes). In at least one exemplary embodiment, the plurality of probes are incorporated into a helmet or skull cap worn by the subject.

A contrast-reversing checkerboard block paradigm was used to stimulate the visual cortex of the subject. This type of visual stimulus is a robust test that reliably produces a response independent of cognitive or learning processes. Each study consisted of 31 alternating control and checkerboard blocks beginning and ending with a control block. During a checkerboard block, an 8 square×8 square black-and-white checkerboard was displayed for 30 seconds, with the squares alternating from black-to-white or white-to-black every 500 milliseconds. Each square measured 2 cm×2 cm creating a 16 cm×16 cm checkerboard. During a control block, a static gray screen was displayed for 30 seconds.

Data Acquisition: An empirically implemented data acquisition system 154 is schematically illustrated in FIG. 3A, and included a Terason 2000™ ultrasound scanner (available from Teratech Corp., Burlington, Mass., including a processing module/laptop computer 156 and an ultrasound probe 158), a personal computer 160 for displaying the visual stimuli, a personal computer 168 for digitizing the subject's ECG signal, an ECG monitor 162 (a model VSM2™, available from Physio-Control, Redmond, Wash.), and an arbitrary waveform generator 170 (a model 33120A™, available from Agilent Technologies, Palo Alto, Calif.) controlled by the visual stimulation computer (i.e., computer 160) for triggering the ultrasound scanner and ECG digitizer. Leads 164 coupled ECG sensors (not specifically shown) attached to a subject to EGC monitor 162. A data conductor 166 (such as a parallel, serial, or universal serial bus cable, although such data conductors are exemplary, rather than limiting) coupled the output of the ECG monitor (a transistor-transistor logic (TTL) signal coincident with the subject's ECG R-wave) to personal computer 168. A data conductor 172 (such as a parallel, serial, or universal serial bus cable, although such data conductors are exemplary, rather than limiting) coupled personal computer 160 to arbitrary waveform generator 170.

The Terason 2000™, a laptop-based, general-purpose ultrasound scanner, with a 4V2 phased array scanhead (90° sector angle, 64 element, 2.5 MHz center frequency, 10 MHz RF sampling frequency, 128 scanlines per frame, and an approximately 55% fractional bandwidth B-mode pulse) was used for ultrasound acquisition. With software provided by the manufacturer, a series of post-beamformed ultrasound radio frequency (RF) frames were collected during B-mode imaging for offline analysis in MATLAB™ (available from The Mathworks, Inc., Natick, Mass.). A total of 240 frames of RF ultrasound were recorded at 30 frames per second from 10 seconds to 18 seconds within each block. While the Terason ultrasound scanner is able to record up to 300 frames of RF ultrasound, in these studies only 240 frames were recorded, to allow sufficient time to write the data to the ultrasound scanner's hard drive. Data collection was started 10 seconds into each block to allow sufficient time for the blood flow to change in response to the neuronal stimulation, based on earlier studies indicating that an 8-10 second lag time was desirable. To automate the data collection on the Terason, an automation application (AutoHotkey™) was used to trigger the ultrasound scanner and save data at appropriate times, without requiring user intervention once the session was started.

A MATLAB™ script running on the Dell Corp. Latitude D610™ laptop computer (i.e., computer 160) was used to display the visual stimuli and synchronize data acquisition by the other two computers (i.e., laptop computer 156 and computer 168), as is schematically illustrated in FIG. 4. Ten seconds into each stimulus block, the MATLAB™ script instructed the arbitrary waveform generator to output a 100 millisecond TTL pulse that triggered the Terason (using the Terason's ECG triggering feature), and the ECG digitizer computer. The subject's ECG R-wave signal was digitized using a Measurement Computing (Middleboro, Mass.) PCI-DAS 1000™ 12-bit digitizer sampling at 1 kHz. Eight seconds after each trigger, the two computers recorded their data to hard drives and rearmed before the next trigger.

It should be recognized that a purpose built system could employ fewer controllers than the empirical system, which was developed using readily available parts. Using a signal controller would eliminate the need for arbitrary waveform generator 170, which is utilized to synchronize ultrasound laptop computer 156 and personal computer 168, to make sure the two computers were acquiring data at the same time. It should also be recognized that controllers other than personal computers can be employed (such as custom processing circuits); personal computers simply represent a readily available type of controller, and are thus exemplary, rather than limiting.

It should also be noted that the cardiac cycle could be identified using a technique other than collecting ECG data (for example, blood pressure data might be used instead). Furthermore, it should be noted that in this empirical study the ultrasound acquisition was not synchronized to the cardiac cycle. Resampling, which is described below, was performed offline after the ultrasound data were collected to correlate the ultrasound data with the cardiac cycle. The resampling function could be eliminated if ultrasound acquisition was synchronized to the cardiac cycle. This approach would also require synchronizing the stimulus with the cardiac cycle. While such an embodiment is certainly encompassed by the disclosure herein, resampling represents a simpler solution, when compared to synchronization. Thus, the ECG monitor (and corresponding computer) are not strictly required, as other techniques do exist for obtaining the desired cardiac signal.

FIG. 3B schematically illustrates a more streamlined system 174, which includes an ultrasound data collection component 176 configured to collect the required ultrasound data, a stimulus component 178 configured to provide the stimulus, a cardiac cycle collection component 180 configured to obtain cardiac cycle data (using ECG or some other technique, as noted above), and at least one controller 182 implementing the steps described herein for using TPI to map brain function. While ultrasound data collection component 176 and cardiac cycle collection component 180 are shown as different components, it should be recognized that in some embodiments ultrasound could be used to estimate the cardiac cycles, such that ultrasound data collection component 176 and cardiac cycle collection component 180 are the same component (or that two different ultrasound components are employed, one to collect TPI data and the other to collect cardiac data).

The data collection and analysis steps are shown in FIG. 5 (which corresponds to the method steps of the flowchart of FIG. 1B optimized for using TPI to map brain function). It should be recognized that the specific method steps of FIG. 5 are exemplary, rather than limiting. Thus, different processing steps (such as different transforms, different types of correlation, different types of filtering, and different steps to identify motion associated with mental stimulation) can alternatively be employed within the scope of this novel approach.

Before discussing the steps in greater detail, the following provides a brief summary of flowchart 184 of FIG. 5. In a block 186 ECG data is collected to identify the cardiac cycle of the subject (although it should be noted that cardiac cycle data can be collected using techniques other than ECG, as discussed herein). In a block 188 post beam formed ultrasound data from brain tissue is collected. In a block 190 a Hilbert transform is performed on the ultrasound data. It should be noted that the step of block 190 is intended to represent converting RF data from real signals to analytic signals. The use of the Hilbert transform in particular is intended to be exemplary, rather than limiting. In a block 192 the ultrasound data undergoes a 2D autocorrelation process. It should be recognized that correlation techniques are a function of the type of transducer employed to collect the ultrasound data. Thus, the specific correlation technique identified in FIG. 5 was selected based on the transducer employed in the empirical studies and is thus intended to be exemplary, rather than limiting. In the empirical study, the correlation step defined the sample volume dimensions as 10 samples of 0.8 mm with a 50% overlap, and 2 scan lines (1.4 degrees) with 0% overlap. Again, such parameters are exemplary, rather than limiting.

In a block 194 the correlated ultrasound data is filtered to separate out a cardiac portion of the signal from a respiratory portion of the signal. As noted above, the respiratory portion is likely to include desired data, but is inherently noisier than the cardiac portion of the signal, thus less signal processing was required to extract useful data from the cardiac portion. The respiratory portion of the signal primarily corresponds to venous pulsations, while the cardiac portion primarily corresponds to arterial pulsations. However, the concepts disclosed herein extend to the use of the respiratory signal portion as well as the cardiac portion of the signal. Given sufficient signal processing techniques to extract noise from the respiratory signal, the respiratory signal alone may be useful.

In a block 196 various signal enhancements are implemented, including waveform segmentation, waveform resampling, and waveform tapering. The purpose of such techniques is to obtain a consistent signal (i.e., to minimize variations between individual signals). Such steps are particularly useful in dealing with variations induced by irregularities in the cardiac cycles (i.e., cardiac cycles are similar but not always identical). Exemplary, but not limiting implementation include segmenting the data into cardiac cycles, re-sampling such that the beginning of each cardiac cycle coincides with its ECG QRS component, and tapering each cardiac cycle to 1 second using a modified, asymmetric Hann window. It should be recognized that other signal processing techniques can be implemented to similarly enhance the data. Furthermore, resampling is not required if the ultrasound data acquisition is synchronized to the cardiac cycle.

In a block 198 the enhanced data undergoes a Principal Components Analysis (PCA); the purpose of which is to analyze the data to identify features that can be used to differentiate the waveforms for the relaxed data from the waveforms for the stimulated data. PCA thus represents an exemplary, but not limiting technique that can be used to parameterize the waveforms (such a step is generally referred to as "parameter extraction"). PCA involves looking at a plurality of signal components, and it should be recognized that parameter extraction may be limited to only one signal component, as opposed to a plurality of signal components. Referring to PCA specifically, after segmentation, re-sampling, and tapering, the waveform for each cardiac cycle can be treated as variable with 31 dimensions, one for each time point in the waveform. Because waveforms are highly correlated, PCA can be used to reduce the dimensionality of the data to significantly fewer dimensions (in empirical studies PCA has been used to reduce dimensionality to as few as 3-5 dimensions, but that may not be true for all cases). This provides greater statistical power with fewer degrees of freedom.

In a block 200, a one-way Multivariate Analysis of Variance (MANOVA) is performed, the purpose of which is to measure statistical differences between rest waveforms and stimulated waveforms for each sample volume. MANOVA thus represents an exemplary, but not limiting technique that can be used to measure such differences.

Displacement Estimation: Referring to FIG. 5, the analytic versions of the post-beamformed RF ultrasound signals were first calculated using the Hilbert transform. From the analytic signals, tissue displacement was measured using a 2-D autocorrelation estimator. The standard one-dimensional (1-D) autocorrelator estimates the mean change in phase of the quadrature demodulated or analytic signal in slow-time, i.e. pulse-to-pulse, and scales the result by the wavelength of ultrasound at a reference frequency, typically the transmitted ultrasound center frequency, to derive velocity or displacement. A limitation of this technique is that the result is biased by the stochastic variation of the ultrasound center frequency and frequency-dependent attenuation. The 2-D autocorrelator additionally estimates the mean change in phase of the signal in fast-time, i.e. depth-to-depth, to calculate the local ultrasound center frequency, and uses the wavelength at that frequency to derive velocity or displacement. For the 2-D autocorrelator, displacement is estimated as:

$$\hat{d}_{2D} = \frac{c}{2} \frac{\frac{1}{2\pi}\arg\{\hat{R}_a(0, T)\}}{\frac{1}{2\pi t_s}\arg\{\hat{R}_a(t_s, 0)\}} \quad (1)$$

where c is the speed of ultrasound in soft tissue, T is the pulse-to-pulse sampling period, $t_s$ is the depth-to-depth sampling period, $\hat{R}_a$ (r, τ) is the estimate of the complex 2-D autocorrelation function at depth lag r and temporal lag τ, and "arg" is the argument, i.e. phase angle, of $\hat{R}_a$ (r, τ).

If the complex autocorrelation is expanded, Eq. (1) for a particular sample volume with a depth lag of one sample and with a temporal lag of one sample can be written as:

$$\hat{d}_{2D} = \frac{c}{2} \frac{\frac{1}{2\pi}\arg\left(\sum_{i=1}^{I}\sum_{j=1}^{J}\sum_{k=2}^{K} Z(i,j,k)Z*(i,j,k-1)\right)}{\frac{1}{2\pi t_s}\arg\left(\sum_{i=2}^{I}\sum_{j=1}^{J}\sum_{k=1}^{K} Z(i,j,k)Z*(i-1,j,k)\right)} \quad (2)$$

where Z is the analytic signal indexed by depth i, scan line j, and frame k, and where I, J, and K indicate the number of depths, scan lines, and frames, respectively, over which the measurement is made. For the empirical studies discussed herein, the values employed are as follows: I=10 (0.77 mm), J=2 (0.025 rad), and K=2 (frames). Displacement for the first frame was set to 0, and displacement for subsequent frames was calculated from the cumulative displacement from previous frames.

Data Conditioning: The displacement waveforms for all of the sample volumes were first forward and reverse filtered to remove respiratory motion using a $3^{rd}$ order, high-pass Butterworth IIR filter with a cutoff at three-quarters of the mean cardiac frequency during the 8 second data block. Mean cardiac frequency was calculated from the subject's ECG R-wave intervals recorded concurrently with the ultrasound data. In some exemplary embodiments, both a cardiac filter and respiratory filter are employed. In other exemplary embodiments, either a cardiac filter or a respiratory filter is employed. The use of a respiratory filter is likely to be beneficial for studying tissue oxygenation in the brain.

Using the ECG R-waves, the displacement waveforms were segmented into their individual cardiac cycles and re-sampled, as schematically illustrated in FIGS. 6A-6C. FIG. 6A represents an exemplary 8 second displacement waveform 202 during a control block for a sample volume near the brain stem after filtering to substantially reduce the effect of respiratory motion. Vertical dotted lines 204 indicate the beginning of the cardiac cycles based on the ECG R-waves. FIG. 6B graphically represents a modified 31 sample Hann window. FIG. 6C graphically represents one cardiac cycle (as indicated by a solid line 206) from FIG. 6A and the waveform after tapering (as indicated by a dotted line 208).

Each cardiac cycle was segmented using the last sample preceding its R-wave and the first sample following the next cardiac cycle's R-wave. Cardiac cycles that began 0.5 seconds into the data block or that ended 0.5 seconds from the end of the data block were not used because of start-up and ending transient effects introduced by the respiratory filter, typically leaving five or six complete cardiac cycles during each block. The segments were then re-sampled by linear interpolation at 30 Hz such that the first time point in each re-sampled displacement waveform coincided in time with the cycle's R-wave. Each re-sampled segment was shifted such that the displacement at the beginning of the cardiac cycle was 0.

Each displacement waveform segment for each cardiac cycle was tapered to 1 second to compensate for the variable durations of the cardiac cycles, to enable all of the cardiac cycles to be compared as described in subsequent sections. A modified 31 sample Hann window was used to taper the displacement waveforms (see FIG. 6B). The first 11 samples within each segment were tapered using the first 11 points of a 21-point Hann window, and the remaining 20 samples were tapered using the last 20 points of a 40 point Hann window. This window was created such that the peak of the windowing function approximately coincided with the systolic peak in the displacement waveform segments. The displacement waveform segments for cardiac cycles less than 1 second long were zero-padded before tapering. Both subjects have resting heart rates less than 60 beats-per-minute, so relatively few cycles needed to be zero-padded. The displacement waveforms were then spatially filtered using a Gaussian filter with a full-width-at-half-maximum (FWHM) of 4 mm.

Feature Extraction and Statistical Analysis: Multivariate Analysis of Variance (MANOVA) applied independently to each sample volume was used to test the null hypothesis that the means of the groups of displacement waveforms collected during the control blocks and stimulus blocks were the same. Before applying MANOVA, Principal Components Analysis (PCA) was used to reduce the dimensionality of the data.

PCA is standard statistical technique commonly used for feature extraction and data reduction. PCA is a linear transform that projects multivariate data onto new coordinate axes, i.e. new variables, which are ordered by the amount of variance in the original data that they explain. If the original variables are highly correlated, the number of variables can be reduced by eliminating the new variables that do not account for a significant fraction of the variance.

The displacement waveforms for each sample volume were first organized into an M row by N column matrix, X, where M corresponds to the number of samples in each cardiac cycle and N corresponds to the number of cardiac cycles from all blocks for the entire study. A typical study consisted of 150 to 170 cardiac cycles. For this analysis, the displacement waveform for each cardiac cycle was treated in effect as a variable with 31 dimensions (M=31). Each row's mean was subtracted to yield the mean-corrected matrix, B, from which the covariance matrix, C, was calculated:

$$C = \frac{1}{N-1} B \cdot B'. \qquad (3)$$

The eigenvector matrix, V, and the eigenvalue matrix, D, of C were then calculated:

$$C \cdot V = V \cdot D \qquad (4)$$

where D is the M×M diagonal matrix of eigenvalues sorted in descending order where each eigenvalue indicates the variance of the original data when projected onto the corresponding eigenvector arranged in columns in the M×M matrix V. The cumulative fractional energy in the first L eigenvectors is defined as:

$$g[L] = \frac{\sum_{l=1}^{L} D[l,l]}{\sum_{m=1}^{M} D[m,m]}. \qquad (5)$$

The cumulative fractional energy can be used for dimensionality reduction by retaining the first L eigenvectors needed to exceed a variance threshold for g. For this work, a threshold of 95% was used. A new M×L matrix, W, was constructed containing the first L eigenvectors. Lastly, the original data were projected onto W:

$$Y = W' \cdot B \qquad (6)$$

where Y is the L×N matrix of principal components, i.e., Y[l,n] corresponds to the projection of the $n^{th}$ displacement waveform onto the $l^{th}$ eigenvector.

The principal components were then divided into two groups, the control group and the checkerboard group, and one-way MANOVA was used to test the null hypothesis that the groups have the same means. Reducing the number of variables by PCA before MANOVA has two benefits. Uncorrelated noise is expected to have a larger spread across the eigenvalue spectrum, so eliminating lower variance eigenvectors improves the signal-to-noise ratio (SNR) of the data. Additionally, reducing the number of variables reduces the degrees of freedom thereby enhancing the statistical power of MANOVA.

RESULTS: Displacement waveforms for two control blocks (control waveforms 212) and two checkerboard blocks (stimulus waveforms 210) for one sample volume are shown in FIG. 7A. The displacement waveforms in FIG. 7A are for four successive blocks. The waveforms have been resampled, tapered to 1 second, and placed end-to-end. The entire data set included 31 blocks and 157 cardiac cycles. Within blocks and across blocks, the overall amplitude varies considerably due primarily to the influence of respiration on cardiac filling and resulting ejection fraction.

FIG. 7B graphically illustrates mean waveforms from all the cardiac cycles for the control blocks (mean control waveform 212A) and all the checkerboard blocks (mean stimulus waveform 210A) for the sample volume. In this sample volume, the p-value used for testing the hypothesis that the control blocks and checkerboard blocks have the same means was $1.0e^{-10}$. The shapes are remarkably similar, but the amplitude of the mean checkerboard waveform is larger than the amplitude of the mean control waveform, as would be expected if the blood flow, and thereby, the tissue pulsatility, increases during visual stimulation.

Large regions of statistically significant activation during visual stimulation were detected in 4 of 7 studies for the male subject and in 3 of 7 studies for the female subject. For both subjects, the active regions consistently spanned the region around the pineal body (posterior P2 segment of the Posterior Cerebral Artery) and the tissue extending posteriorly along the mid-line (P3 and P4 segments of the Posterior Cerebral Artery). FIG. 8 shows the consistency in the results from the four successful studies for the male subject. The p-values calculated by MANOVA are shown super-imposed on B-mode images for p-values less than 0.01. FIG. 9 shows the p-values for one of the sessions superimposed on an MRI image slice corresponding approximately to the ultrasound image plane.

Referring to FIG. 8, the left column includes B-mode images from one frame collected during each session. The brightest echo in each image at a depth of 80 mm is from the region around the pineal body. The right column shows the p-values for the functional TPI data superimposed on the respective B-mode images. P-values less than 0.01 are not considered significant and are not shown. A heavy boundary 214 in the images in the right column indicates the region-of-interest for the functional TPI analysis.

Referring to FIG. 9, an MRI slice is shown, the slice approximately corresponding to the ultrasound image plane with superimposed p-values from the male subject, for session 5. The functional TPI p-values have been drawn as a contour plot with curves every order of magnitude from $10^{-9}$ to $10^{-3}$. The following structures are identified in FIG. 9: pineal body 142, posterior commisure 144, quadrigeminal cistern 148, and $3^{rd}$ ventricle 146.

DISCUSSION: The empirical studies demonstrated a statistically significant increase in tissue pulsatility within the posterior region of the brain in response to a visual stimulus. The active regions appear to correlate with the paths of vessels that supply the visual cortex. A positive response was obtained in four out of seven studies for the male subject and in three out of seven studies for the female subject. The lack of response in the remaining studies could potentially be attributed to attentiveness, since prior brain function mapping studies have demonstrated a greater vascular response to a visual stimulus during periods of increased attentiveness. The study required the subject to lay still in a prone position with his/her head supported within a massage table face donut. Both subjects expressed difficulty staying awake, lack of attentiveness, and fogging or tearing of the eyes at times. Passive viewing may not generate a sufficiently large response to be consistently detected by the empirical system. To compensate for this, future systems and studies can introduce a task that requires attentive interaction, such as a reading test or a symbol matching test. Although both of these tasks would activate regions in addition to the visual cortex, if the response is more repeatable, such results would indicate that attentiveness is an issue.

The ultrasound system used for the study may also have contributed to the variability in the response. A commercially available system with a phased array transducer that was not optimized for transcranial imaging was used. Therefore, the frequency and power settings are not optimized for this specific application. Furthermore, the transducer was a standard hand-held transducer retained by an articulated clamp. Although relatively stable, the long moment arm introduced some mechanical instability. An ultrasound system with a fitted transducer would be more appropriate and would enable the transducer to be held in place with a helmet-style fixture, so the subject could sit in a more comfortable position during a study.

Because functional TPI is based upon ultrasound, it maintains the qualities of being a rapid, portable, inexpensive tool that can be used for continuous monitoring and for repeat studies. The advantage of functional TPI over functional TCD is the use of tissue rather than blood as the signal source. Ultrasound backscatter from tissue is significantly stronger than that from blood, enabling acquisition of ultrasound signals of the cortical region of interest directly through the overlying skull. An additional advantage is the ability of this approach to study small functional cortical regions rather than larger arteries that supply multiple functional regions. In the empirical study described above, ultrasound scanning was performed through the skull over the occipital protuberance, to ensure that the scans would be imaging through the visual cortex in the occipital lobe. The use of a tissue rather than a blood backscatter signal may also result in an overall reduction in transmitted ultrasound power once the technique is optimized. The highest power output allowed by the FDA for diagnostic imaging is for TCD.

Additional work is being done to determine if tissue pulsatility is more appropriately measured using tissue strain rather than tissue displacement. Assessing regional brain activity using displacement is complicated by the cumulative motion of the brain, i.e. an increase in blood flow to a stimulated region of the brain may displace remote tissues, making it appear as if they are activated even though they are not. Strain imaging could theoretically compensate for this remote, common-mode movement. Limited, preliminary analysis using strain waveforms measured using a least-squares strain estimator reveals similar regions of activation, suggesting cumulative tissue displacement is not a significant problem.

CONCLUSIONS: The empirical study showed that functional TPI is a potential technique for functional brain imaging. The light weight and small size of ultrasound scanners will enable functional brain imaging studies in ambulatory patients, a freedom not available to functional MRI and nuclear imaging methods. Although functional EEG methods have comparable cost and portability, EEG lacks the spatial resolution of ultrasound. The electrical brain activity signals of EEG methods including evoked response potentials are complementary to the blood perfusion signals provided by the functional TPI.

Significantly, the empirical study consistently observed regions of significantly increased tissue pulsatility extending posteriorly from the region of the pineal body to the occipital lobe through which pass the segments of the Posterior Cerebral Artery that perfuse the primary visual cortex.

The Use of TPI to Monitor Cerebral Vasoreactivity: In addition to using TPI to map brain function, empirical studies have also been performed to evaluate TPI's ability to monitor cerebral vasoreactivity (reduced cerebral vasoreactivity is associated with many medical conditions, and a system and a procedure for monitoring cerebral vasoreactivity comprise a useful diagnostic tool).

As with other perfused tissues, changing blood volume causes the brain to expand and relax over the cardiac cycle. Because the volume of the brain is constrained by the fixed volume of the skull, expansion of the brain early in the cardiac cycle compresses the cerebral ventricles forcing cerebrospinal fluid (CSF) out of the skull. Later in the cardiac cycle, brain blood volume decreases, drawing CSF back into the skull. This expansion of the brain and compression of the cerebral ventricles causes the brain to move medially during systole and laterally during diastole. Additionally, the changing blood volume pushes the brain posteriorly and caudally towards the foramen magnum during systole followed by a rebound during diastole.

Cerebral vasoreactivity (CVR) is the ability of the cerebral arterioles to respond to changes in arterial $CO_2$ partial pressure ($PaCO_2$) in order to regulate blood flow and oxygen delivery to the brain. Under normal conditions, hypercapnia, an increase in $PaCO_2$, will cause the cerebral arterioles to dilate, reducing vascular resistance and increasing cerebral blood flow (CBF). Hypocapnia, a decrease in arterial $PaCO_2$, will cause the cerebral arterioles to constrict, increasing vascular resistance and reducing CBF.

Cerebral vasoreactivity is most commonly tested by having subjects breathe increasing concentrations of $CO_2$ or by administering acetazolamide to increase $PaCO_2$, or by having subjects voluntarily hyperventilate to decrease $PaCO_2$. Measurement of CVR has been used to evaluate cerebral vascular function over a broad range of clinical applications, including monitoring the severity of brain damage after an ischemic event, predicting the risk of a cerebral ischemic event in patients with carotid occlusive disease, assessing the efficacy of a carotid endarterectomy, and studying anxiety disorders and migraine attacks.

MRI, PET, and NIRS techniques have all been used to monitor changes in CBF with changes in $PaCO_2$. The most common method used to assess CVR is TCD, which provides a low-cost, non-invasive means to measure blood flow velocities in the larger cerebral blood vessels in real-time.

The following discussion describes an empirical study conducted to test the feasibility of using TPI to assess CVR. Brain tissue pulsatility was measured in four subjects through the temporal acoustic window using a standard, general-purpose ultrasound scanner. Tissue pulsatility was measured before, during, and after voluntary hyperventilation, and the results were correlated with the subjects' end-tidal $CO_2$ measurements collected concurrently with ultrasound acquisition.

It should be noted that correlation with the subjects' end-tidal $CO_2$ measurements is optional and not inherently required. This correlation was employed in an exemplary embodiment to determine whether TPI can be used to assess CVR. If the studies documented a poor statistical correlation, the study would suggest that TPI could not be used to monitor CVR. Thus, TPI data that are not correlated with end-tidal $CO_2$ can be used to assess CVR trends. Such an assessment would be qualitative rather than quantitative. If a quantitative assessment is desired, then end-tidal $CO_2$ would be required. Thus, the use of TPI to monitor CVR encompasses both qualitative monitoring without correlation to end-tidal $CO_2$, and quantitative monitoring in connection with correlation to concurrently acquire end-tidal $CO_2$ data.

Furthermore, the comments made above with respect to employing other techniques to collect cardiac cycle data for using TPI to map brain function also apply to using TPI to monitor CVR. Thus, the use of ECG data in the following disclosure is intended to be exemplary, rather than limiting. Similarly, re-sampling of the TPI data would not be required if ultrasound acquisition was synchronized to the cardiac cycle.

Subjects: Four subjects, all male, ages 29, 33, 41, and 52, participated in the study. No effort was made to control the day of the week, time of day, or caffeine intake when the tests were made. Written informed consent was obtained from all subjects.

Protocol: During a study, the subject lay supine on a massage table (available, for example, from Stronglite Inc., Cottage Grove, Oreg.) with the head of the subject stabilized in a custom-built, padded fixture. Before the study, ECG leads were attached to the subject's arms, and a cannula was placed in the nostrils to collect expired air. A Terason 4V2™ phased-array transducer (available from Teratech Corp., Burlington, Mass.) held by an articulated clamp (available, for example, from Manfrotto, Bassano del Grappa, Italy) securely mounted to the table was positioned over the right ultrasound temporal window, slightly anterior to and superior to the ear of the subject. Before locking the clamp in place, the transducer was positioned by an experienced sonographer to image a nearly transverse plane through the cerebral peduncles.

Each study consisted of three phases, a pre-hyperventilation phase lasting 6 minutes and 40 seconds, a voluntary hyperventilation phase lasting 20 minutes, and a post-hyperventilation phase lasting 20 minutes. During the pre and post-hyperventilation phases, the subject was instructed to breathe normally through his nostrils to maintain an end-tidal $CO_2$ around 40 mm Hg. During the hyperventilation phase, the subject was instructed to breathe rapidly (approximately one breath every 2 seconds) through his nostrils to maintain an end-tidal $CO_2$ around 20 mm Hg. Although not explicitly instructed to do so, subjects maintained a relatively constant depth of respiration throughout the hyperventilation phase.

Data acquisition: An empirically implemented data acquisition system 216 is schematically illustrated in FIG. 10A. Note that system 216 shares components with system 154 of FIG. 3A, and common components share common reference numerals. System 216 includes a Terason 2000™ laptop-based, general-purpose ultrasound Scanner (available from Teratech Corp., Burlington, Mass., including processing module/laptop computer 156 and ultrasound probe 158), personal computer 168a with a Measurement Computing (Middleboro, Mass.) PCI-DAS 1000™ 12-bit digitizer sampling at 1 kHz for recording the subject's ECG and end-tidal $CO_2$ signals, ECG monitor 162 (VSM2™, Physio-Control, Redmond, Wash.), arbitrary waveform generator 170 (model 33120A™, available from, Agilent Technologies, Palo Alto, Calif.) for triggering the ultrasound scanner (i.e., computer 156) and the digitizer (i.e., computer 168a), and a $CO_2$ monitor 220 (model Capnocheck Plus 9004™, available from Smiths Medical PM, Inc., Waukesha, Wis.). Leads 164 coupled ECG sensors (not specifically shown) attached to a subject to EGC monitor 162. A data conductor 166 (such as a parallel, serial, or universal serial bus cable, although such data conductors are exemplary, rather than limiting) coupled the output of the ECG monitor (a transistor-transistor logic (TTL) signal coincident with the subject's ECG R-wave) to personal computer 168a. A data conductor 222 (such as a parallel, serial, or universal serial bus cable, although such data conductors are exemplary, rather than limiting) coupled personal computer 168a to $CO_2$ monitor 220, which receives input from a nasal cannula 218.

It should be noted that $CO_2$ monitor 220 was employed in system 216 to determine if there was a correlation between TPI pulse amplitude data and subject end-tidal $CO_2$. As discussed below, such a correlation exists, indicating that TPI pulse amplitude data can be used to monitor CVR. Where end-tidal $CO_2$ data are available, the TPI pulse amplitude data can be calibrated with the end-tidal $CO_2$ data, such that TPI data can quantitatively assess CVR. Absent such calibration, the TPI data is likely able to provide a qualitative assessment of CVR. Such calibration will require some measurement of the concentration of $CO_2$ in the subject's blood. An end-tidal $CO_2$ monitor is an easy way to do that. One could also draw blood and measure $CO_2$ concentration directly. Alternatively, one could have the subject breathe gas with excess $CO_2$ rather than have them hyperventilate as was employed in the empirical study. In that case, the $CO_2$ concentration in blood is determined by the concentration of $CO_2$ the subject is breathing and one would not need to measure the concentration of $CO_2$.

It should be recognized that in addition to having a subject hyperventilate or breathe air with excess $CO_2$ to place the patient in a stimulated state, a pharmacological agent (such as acetazolamide) could be administered to alter a concentration of carbon dioxide in the patient's blood.

FIG. 10B schematically illustrates a more streamlined system 230. Note that system 230 shares components with system 174 of FIG. 3B, and common components share common reference numerals. System 230 includes an ultrasound data collection component 176 configured to collect the required ultrasound data, a cardiac cycle collection component 180 configured to obtain cardiac cycle data (using ECD or some other technique, as noted above), an optional $CO_2$ concentration data collection component 232 (required if a quantified assessment of CVR is desired, and not required for a qualified assessment of CVR) and at least one controller 182a implementing the steps described herein for using TPI to monitor CVR. As noted above, in at least one embodiment ultrasound is employed to estimate the cardiac cycle, and ultrasound data collection component 176 and cardiac cycle collection component 180 can be implemented using an ultrasound system.

The 4V2 phased array scanhead (90° sector angle, 64 element, 2.5 MHz center frequency, 10 MHz RF sampling frequency, 128 scanlines per frame, and approximately 55% fractional bandwidth B-mode pulse) was used for ultrasound acquisition. With software provided by the manufacturer, a series of post-beamformed ultrasound RF (radiofrequency) frames were collected during B-mode imaging for off-line analysis in MATLAB™ (The Mathworks, Inc., Natick, Mass.). The arbitrary waveform generator was programmed to output a 100 millisecond TTL pulse once every 40 seconds to trigger the digitizer and ultrasound scanner using the ultrasound scanner's ECG triggering feature. With each trigger, 240 frames of RF ultrasound were collected at 30 frames per second, which corresponds to 10, 30, and 30 data sets that were collected before, during, and after hyperventilation, respectively. To automate the data collection by the ultrasound scanner, an automation application (AutoHotkey™) was used to trigger the ultrasound scanner and save data at the appropriate times without user intervention, once the study was started.

Note that the arbitrary waveform generator was used because the ultrasound data and the ECG data were collected with two different computers. The arbitrary waveform generator was used to synchronize the two computers, to ensure that the two computers were acquiring data at the same time. If a single logical controller were employed, the waveform generator would not be required.

The data collection and analysis steps are shown in flowchart 185 of FIG. 11 (which corresponds to the method steps of the flowchart of FIG. 1B optimized for using TPI to monitor CVR). It should be recognized that the specific method steps of FIG. 11 are exemplary, rather than limiting. Thus, different processing steps (such as different transforms, different types of correlation, different types of filtering, and different steps to identify motion associated with mental stimulation) can alternatively be employed within the scope of this novel approach. Note that flowchart 185 shares steps with flowchart 184 of FIG. 5, and common steps share common reference numerals.

Before discussing the steps in greater detail, the following provides a brief summary of flowchart 185 of FIG. 11. In a block 186 ECG data is collected to identify the cardiac cycle of the subject (although it should be noted that cardiac cycle data can be collected using techniques other than ECG, as discussed herein). In a block 188 post beam formed ultrasound data from brain tissue is collected. In a block 190 a Hilbert transform is performed on the ultrasound data. It should be noted that the step of block 190 is intended to represent converting RF data from real signals to analytic signals. The use of the Hilbert transform in particular is intended to be exemplary, rather than limiting. In a block 192 the ultrasound data undergoes a 2D autocorrelation process. It should be recognized that correlation techniques are a function of the type of transducer employed to collect the ultrasound data. Thus, the specific correlation technique identified in FIG. 11 was selected based on the transducer employed in the empirical studies and is thus intended to be exemplary, rather than limiting. In the empirical study, the correlation step defined the sample volume dimensions as 10 samples of 0.8 mm with a 50% overlap, and 2 scan lines (1.4 degrees) with 0% overlap. Again, such parameters are exemplary, rather than limiting.

In a block 194 the correlated ultrasound data is filtered to separate out a cardiac portion of the signal from a respiratory portion of the signal. As noted above, the respiratory portion is likely to include desired data, but is inherently noisier than the cardiac portion of the signal, thus less signal processing was required to extract useful data from the cardiac portion. The respiratory portion of the signal primarily corresponds to venous pulsations, while the cardiac portion primarily corresponds to arterial pulsations. However, the concepts disclosed herein extend to the use of the respiratory signal portion as well as the cardiac portion of the signal. Given sufficient signal processing techniques to extract noise from the respiratory signal, the respiratory signal alone may be useful.

In a block 197 various signal enhancements are implemented, including waveform segmentation, waveform resampling, and waveform averaging. The purpose of such techniques is to obtain a consistent signal (i.e., to minimize variations between individual signals). These steps are discussed in greater detail below. Note that these enhancements steps are not identical to those performed for using ultrasound data to map brain function, particularly with respect to the averaging technique.

In a block 199 the enhanced data is manipulated to measure pulse amplitude for the relaxed data and the stimulated data. The theory behind using TPI to assess CVR is based on correlating pulse amplitude to end-tidal $CO_2$.

In a block 201, a first order linear regression is performed on pulse amplitude and end-tidal $CO_2$ data.

Data Analysis: It should be noted that the specific transform functions, correlation functions, filtering, signal enhancements, and signal analysis steps of FIG. 11 are exemplary, rather than limiting. The analytic versions of the post-beamformed RF ultrasound signals were first calculated using the Hilbert transform. From the analytic signals, tissue displacement was calculated using the 2-D autocorrelation estimator, which estimates the mean change in phase of the quadrature-demodulated or analytic signal in slow-time, i.e., pulse-to-pulse, as well as fast-time, i.e., depth-to-depth. If multiple scan lines are included in the calculation, the displacement for a particular sample volume can be written as:

$$\hat{d}_{2D} = \frac{c}{2} \frac{\frac{1}{2\pi}\arg\left(\sum_{i=1}^{I}\sum_{j=1}^{J}\sum_{k=2}^{K} Z(i,j,k)Z*(i,j,k-1)\right)}{\frac{1}{2\pi t_s}\arg\left(\sum_{i=2}^{I}\sum_{j=1}^{J}\sum_{k=1}^{K} Z(i,j,k)Z*(i-1,j,k)\right)} \quad (7)$$

where "arg" is the argument, i.e., phase angle, of the autocorrelation function, c is the speed of ultrasound, $t_s$ is the depth-to-depth sampling period, Z is the analytic signal indexed by depth i, scan line j, and frame k, and where I, J, and K are the number of depths, scan lines, and frames, respectively, over which the measurement is made. The following parameters were used in this study: I=39 (3.00 mm), J=2 (0.025 rad), and K=2 (frames). Displacement for the first frame was set to 0, and displacement for subsequent frames was calculated from the cumulative displacement from previous frames.

The displacement waveforms for all of the sample volumes for each data set were first forward and reverse filtered using a sixth-order, bandpass Butterworth IIR filter with a bandpass between three-quarters and five times the mean cardiac frequency, which was calculated for each data set from the subject's ECG R-wave intervals recorded concurrently with the ultrasound data. FIG. 12A graphically illustrates a displacement waveform 240 from one dataset from a single sample volume from subject 4 before band-pass filtering. FIG. 12B graphically illustrates displacement waveform 240 of FIG. 12A after filtering, to yield a filtered waveform 242. FIG. 12C graphically illustrates a mean displacement waveform 244 calculated by averaging cardiac cycles from the waveform of FIG. 12B. Vertical dotted lines in FIG. 12B indicate the beginning of each cardiac cycle. The lower frequency limit was selected to remove tissue motion synchronized with respiration which approached 0.5 Hz during the hyperventilation phase while retaining pulsatile tissue motion synchronized with the cardiac cycle, which was typically around 0.9 Hz or greater. The upper frequency limit was selected to minimize higher frequency noise while maintaining the majority of the motion synchronized with the cardiac cycle.

For each sample volume, the displacement waveform was parameterized by its "pulse amplitude", i.e., the displacement of the sample volume during the systolic phase of the cardiac cycle (FIG. 12C). Each displacement waveform was first segmented into its individual cardiac cycles using the ECG R-waves, and each segmented cardiac cycle of displacement was then re-sampled at 30 Hz by linear interpolation such that the first time point in each cycle coincided with its R-wave. The re-sampled displacement waveforms were then averaged to yield a mean displacement waveform for each sample volume. To calculate pulse amplitude, the displacement extrema occurring during the first 0.5 seconds of the mean displacement waveform were identified, and the pulse amplitude was calculated by subtracting the earlier extremum displacement, i.e., the pre-systolic displacement, from the later extremum displacement, i.e., the peak systolic displacement. Positive pulse amplitude indicates displacement towards transducer during systole, and negative pulse amplitude indicates displacement away from the transducer.

The pulse amplitudes for each sample volume across all 70 data sets were then fit to the end-tidal $CO_2$ measurements using first-order linear regression. The maximum end-tidal $CO_2$ recorded during each eight second data set was used to represent the end-tidal $CO_2$ during the data set. The p-value of the linear regression was used to identify sample volumes with pulse amplitudes significantly correlated with the end-tidal $CO_2$ signal. FIG. 13A graphically illustrates end-tidal $CO_2$ from subject 3, along with pulse amplitude measurements from a single sample volume. FIG. 13B graphically illustrates pulse amplitude versus end-tidal $CO_2$ from the same sample volume, along with the best-fit line with first-order linear regression. The term "pa" in the inset equation of FIG. 13B refers to pulse amplitude, and $CO_2$ in the same equation is the end-tidal $CO_2$ measurement.

RESULTS: FIGS. 14A-14C collectively include a B-mode image 248 from one of the subjects along with the pulse amplitudes from two data sets, one collected before hyperventilation when the subject's end-tidal $CO_2$ was 41.7 mm Hg (pulse amplitude 250 of FIG. 14B), and one collected during hyperventilation when the subject's end-tidal $CO_2$ was 20.7 mm Hg (pulse amplitude 252 of FIG. 14C). The images show large regions of brain tissue pulsating up to ±75 μm under normal breathing conditions and a significant reduction in the pulse amplitude during hyperventilation. In both cases, the pulsation is predominantly away from the transducer in the hemisphere closest to the transducer and is towards the transducer in the contra-lateral hemisphere. Specifically, FIG. 14A is a transverse B-mode image of the brain and skull of subject 2. FIG. 14B is a pulse amplitude image of the brain of subject 2 at rest (i.e., before hyperventilation) with an end-tidal $CO_2$ of 41.7 mm of Hg. FIG. 14C is a pulse amplitude image of the brain of subject 2 during hyperventilation with an end-tidal $CO_2$ of 20.7 mm of Hg. A positive-pulse amplitude indicates displacement toward the ultrasound transducer during systole, while a negative-pulse amplitude indicates displacement away from the ultrasound transducer during systole.

FIG. 15 includes B-mode images from all of the subjects along with the predicted percent change in pulse amplitude for a change in end-tidal $CO_2$ from 40 mm of Hg to 20 mm of Hg for sample volumes with linear regression p-values less than 0.01. The B-mode images are from the first frame of the first data set for each subject. The predicted pulse amplitudes at 40 mm of Hg and 20 mm of Hg are calculated using the equation derived for each sample volume from the first-order linear regression of the measured pulse amplitudes onto the end-tidal $CO_2$ signal. Percent change is calculated by subtracting the pulse amplitude at 20 mm of Hg from the pulse amplitude at 40 mm of Hg and dividing the result by the pulse amplitude at 40 mm of Hg. Although some regions of increased pulsatility were observed, tissue pulsatility decreased with decreasing $PaCO_2$ for all subjects in the vast majority of sample volumes with p-values less than 0.01. Specifically, a left column 254 of FIG. 15 includes the B-mode images, while a right column 256 includes the expected percent change in pulse amplitude for a decrease in end-tidal $CO_2$ from 40-20 mm of Hg. Pulse amplitude percent change is shown only for sample volumes where the linear regression p-value of pulse amplitude onto end-tidal $CO_2$ was less than 0.01.

FIG. 16A graphically illustrates histograms of percent changes from the four subjects for sample volumes with linear regression p-values less that 0.01. FIG. 16B graphically illustrates the median, $25^{th}$ and $75^{th}$ percentiles for percent changes for p-values less than 0.01 arranged by subject age. The tissue pulsatility response to hypocapnia appears to decrease with age, although with only four subjects, it is not possible to conclude that this trend is real and significant. This prospective finding is consistent, however, with the results of other studies that indicate a decrease in CVR with age, and age-related cerebrovascular disease.

DISCUSSION: The TPI CVR study demonstrated statistically significant changes in tissue pulsatility in the brain in response to hypocapnia induced by voluntary hyperventilation. In all subjects, the tissue pulsatility predominantly decreased with hyperventilation. There were, however, regions where pulsatility increased and regions without statistically significant changes in pulsatility. With TPI, the ability to accurately resolve tissue motion is affected by the amplitude and direction of motion along with the ultrasound signal-to-noise ratio (SNR). At the beginning of each cardiac cycle, the brain displaces medially towards the ventricles and posteriorly and caudally towards the foramen magnum. As a result, there is a gradient of motion across the brain. The amplitude of displacement is least near the surface of the skull and greatest near the ventricles and the foramen magnum. With conventional Doppler ultrasound, it is only possible to measure the projected component of displacement parallel to the direction of ultrasound propagation. Because the displacement in the brain is not isotropic, the measured displacement will generally be less than the true displacement.

The effect of this limitation is evidenced by the heterogeneity in the magnitude of the pulse amplitude, i.e., the absolute value of the pulse amplitude, between the two hemispheres (see FIGS. 14A-14C). In both the normocapnic and hypocapnic cases, the absolute pulse amplitude measured in the left anterior hemisphere is greater than the absolute pulse amplitude measured in the right anterior hemisphere. It is assumed that corresponding sample volumes in the two hemispheres are displaced with equal magnitudes but in opposite directions in the medial direction. If this assumption is true, it would mean that the angle between the direction of ultrasound propagation and the direction of displacement in the sample volume in the ipsilateral hemisphere (with respect to the ultrasound transducer) would be greater than the angle between the direction of ultrasound propagation and the direction of displacement in the contralateral sample volume, making the measured absolute pulse amplitude less in the ipsilateral sample volume than in the corresponding contralateral sample volume. Assuming that the direction of displacement does not change with hypocapnia, underestimation of the true pulse amplitude by a constant factor would not alter the percent change in pulse amplitude.

As with all ultrasound measurements, the measurement of pulse amplitude and the detection of significant changes in pulse amplitude are influenced by ultrasound SNR. Compared to other locations in the body, the SNR from the brain can be particularly poor, given the significant attenuation of ultrasound by the skull. As SNR decreases, the variance in the pulse amplitude estimate increases. This variance is of greater significance when the true pulse amplitude is small, such as near the surface of the skull. As shown in FIG. 15, all of the subjects have regions without statistically significant changes in pulse amplitude, which is most likely explained by poor SNR and not by a true lack of change in pulse amplitude.

Also evident are regions of statistically significant increases in pulse amplitude with hyperventilation, which in subjects 1 and 3, and less so in subject 2, are concentrated around the posterior temporal lobe. It is unclear if these regions are the result of low SNR, or if the response is real. It has been shown using functional MRI that multiple regions distributed around the brain are activated during voluntary breathing. Furthermore, as described above, it has been shown that TPI can be used to detect a stimulus-evoked regional activation in the brain. Given the limited number of subjects, and given the weak ultrasound signal strength and small pulse amplitudes in this region for all three subjects, it is difficult to conclude that this effect is real, but it is possible that the act of hyperventilating is activating regions of the brain, thereby increasing blood flow to the regions and increasing the local tissue pulsatility.

In addition to the inter-subject variability in mean percent change in pulse amplitude with hypocapnia, which may be attributable to age differences as previously discussed, there are differences in the fractional areas of the subjects' brains with statistically significant changes in pulse amplitude. Some of this seems to be due to differences in the general level of brain pulsatility between the subjects. Statistically significant changes in pulse amplitude were detected in more of subject 2's brain than for any other subject. Pulsatility throughout the brain also tended to be considerably greater before, during, and after hyperventilation in subject 2's brain compared to the other subjects. Because the brain displacement was generally greater in subject 2, thereby decreasing the influence of noise on the measured pulse amplitude, the likelihood of establishing statistical significance was greater.

The ultrasound system used for the study may have also contributed to the heterogeneity of the TPI signal within and between subjects. The ultrasound scanner used was a commercially available system with a phased-array transducer that was not optimized for transcranial imaging. Therefore, the frequency and power settings were not optimized for TPI CVR studies. Furthermore, the transducer was a standard handheld transducer held by an articulated clamp. Although relatively stable, the long moment arm potentially introduced some mechanical instability.

Because TPI is based on ultrasound, it maintains the qualities of being a rapid, portable, inexpensive tool that can be used for continuous monitoring in almost any setting. The advantage of TPI over TCD for assessing CVR is the use of tissue rather than blood as the signal source. Ultrasound backscatter from tissue is significantly stronger than that from blood, which is particularly important when imaging the brain, given the significant attenuation of ultrasound by the skull. Because of this fact, TCD is generally limited to imaging blood flow in the major cerebral blood vessels that supply large portions of the brain. With TPI, the increased ultrasound backscatter from tissue enables ultrasound to image brain displacement as a surrogate for blood flow through locations on the skull other than the three traditional acoustic windows. One potential alternative to both TPI and conventional TCD is transcranial ultrasound using echo-contrast agents. Such an approach would enable better visualization of localized cerebral perfusion, but would increase the cost and complexity of the examination.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. A method for using ultrasound to measure at least one of a tissue displacement in a brain of a subject and a tissue strain in the brain of the subject, for mapping brain function, the method comprising the steps of:
   (a) collecting ultrasound data for the brain while the subject is in a relaxed state, thereby collecting relaxed data, the relaxed data including ultrasound data for one or more first sample volumes within the brain of the subject while the subject is in the relaxed state;
   (b) collecting ultrasound data for the brain while the subject is in a stimulated state, thereby collecting stimulated data, the stimulated data including ultrasound data for one or more second sample volumes within the brain of the subject while the subject is in the stimulated state, the one or more second sample volumes spatially corresponding to the one or more first sample volumes, the stimulated state being achieved in response to application of a mental stimulus selected from a group of stimuli consisting of:
      (i) a first mental stimulus based on motion;
      (ii) a second mental stimulus based on sound;
      (iii) a third mental stimulus based on taste;
      (iv) a fourth mental stimulus based on touch; and
      (v) a fifth mental stimulus based on vision;
   (c) comparing the collected relaxed data to the collected stimulated data, wherein comparing the collected relaxed data to the collected stimulated data includes comparing information indicative of tissue displacement in the one or more first sample volumes with information indicative of tissue displacement in the spatially corresponding one or more second sample volumes;
   (d) identifying, based on the comparison of the collected relaxed data to the collected stimulated data, at least one of (i) tissue displacement in at least one of the one or more second sample volumes within the brain of the subject associated with the application of the mental stimulus and (ii) tissue strain in at least one of the one or more second sample volumes within the brain of the subject associated with the application of the mental stimulus, the identified at least one of tissue displacement and tissue strain being present in the collected stimulated data and absent from the collected relaxed data; and
   (e) correlating the applied mental stimulus with a specific structure in the brain using the identified at least one of tissue displacement and tissue strain present in the collected stimulated data and absent from the collected relaxed data.

2. The method of claim 1, wherein at least one of the steps of collecting the relaxed data and collecting the stimulated data comprises the step of collecting ultrasound data through a portion of a skull of the subject that is not an acoustic window.

3. The method of claim 1, further comprising the steps of:
(a) collecting cardiac cycle data from the subject; and
(b) using the cardiac cycle data to re-sample the relaxed data and the stimulated data before the applied mental stimulus is correlated with the specific structure in the brain.

4. The method of claim 3, further comprising the steps of:
(a) selecting a voxel from a plurality of voxels defined by the collected ultrasound data; and
(b) measuring a peak to peak displacement for each voxel over each cardiac cycle as a metric of pulsatility.

5. The method of claim 4, further comprising the step of identifying voxels from the plurality of voxels having significantly different pulsatilities during the relaxed state and the stimulated state.

6. The method of claim 1, further comprising the step of processing the relaxed data and the stimulated data to prepare the relaxed data and the stimulated data for analysis by filtering out a respiratory portion of the relaxed data and the stimulated data.

7. The method of claim 1, further comprising the step of processing the relaxed data and the stimulated data to prepare the relaxed data and the stimulated data for analysis by implementing waveform segmentation, waveform re-sampling, and waveform tapering of the relaxed data and the stimulated data.

8. The method of claim 1, further comprising the step of processing the relaxed data and the stimulated data to prepare the relaxed data and the stimulated data for analysis by implementing waveform segmentation, waveform re-sampling and waveform averaging of the relaxed data and the stimulated data.

9. The method of claim 1, further comprising the step of performing a principal component analysis to facilitate mapping of brain function.

10. The method of claim 9, further comprising the step of performing a one-way multivariate analysis of variance.

11. The method of claim 1, wherein collecting relaxed data, collecting stimulated data, and application of the mental stimulus are synchronized with a cardiac cycle of the subject.

12. The method of claim 1, further comprising measuring motion due to blood flow associated with the application of the mental stimulus, motion due to cardiac cycles, and motion due to respiration.

13. The method of claim 12, further comprising the step of distinguishing motion due to blood flow associated with the application of the mental stimulus from other types of motion including motion due to cardiac cycles and motion due to respiration, wherein correlating the applied mental stimulus with a specific structure in the brain includes correlating based on the motion due to blood flow associated with the application of the mental stimulus.

14. The method of claim 1, further comprising the step of reordering the collected relaxed data and the collected stimulated data such that a first ultrasound pulse in the data coincides with the beginning of a cardiac cycle of the subject.

15. The method of claim 1, further comprising the steps of:
(a) determining a relaxed-state tissue displacement in the brain of the subject using the collected relaxed data; and
(b) determining a stimulated-state tissue displacement in the brain of the subject using the collected stimulated data;
wherein the step of comparing the collected relaxed data to the collected stimulated data includes comparing the relaxed-state tissue displacement to the stimulated-state tissue displacement, and the step of identifying at least one of tissue displacement and tissue strain includes identifying a difference between the relaxed-state tissue displacement and the stimulated-state tissue displacement.

16. The method of claim 1, further comprising the steps of:
(a) calculating displacement waveforms for a number of sample volumes from the collected relaxed data and the collected stimulated data, the displacement waveforms each indicating an amount of tissue displacement;
(b) filtering the displacement waveforms to remove respiratory motion;
(c) segmenting the displacement waveforms into their individual cardiac cycles;
(d) re-sampling the segmented displacement waveforms such that a first time point in each re-sampled displacement waveform coincides in time with a cardiac cycle's R-wave;
(e) shifting each re-sampled segment such that the displacement at the beginning of the cardiac cycle is zero; and
(f) tapering each displacement waveform segment for each cardiac cycle to a certain time period.

17. The method of claim 16, wherein tapering includes applying a windowing function to at least one of the segmented displacement waveforms such that a peak of the windowing function approximately coincides with the systolic peak in the at least one segmented displacement waveforms.

18. The method of claim 16, further comprising reducing the dimensionality of the tapered displacement waveform segments.

19. The method of claim 16, further comprising measuring statistical differences between (i) the tapered displacement waveform segments generated from the relaxed data and (ii) the tapered displacement waveform segments generated from the stimulated data.

20. The method of claim 19, wherein measuring statistical differences includes:
determining a first mean displacement waveform from (i) the tapered displacement waveform segments generated from the relaxed data;
determining a second mean displacement waveform from (ii) the tapered displacement waveform segments generated from the stimulated data; and
identifying a difference between the first mean displacement waveform and the second mean displacement waveform.

21. A method for using ultrasound to measure at least one of a tissue displacement in a brain of a subject and a tissue strain in the brain of the subject to map a brain function, comprising the steps of:
(a) collecting ultrasound data for the brain while the subject is in a relaxed state, thereby collecting relaxed data, the relaxed data including ultrasound data for one or more first sample volumes within the brain of the subject while the subject is in the relaxed state;
(b) exposing the subject to a stimulus selected to induce a neural stimulus in the brain, thereby placing the subject in a stimulated state, the stimulus having been selected from a group of stimuli consisting of:
  (i) a first neural stimulus based on motion;
  (ii) a second neural stimulus based on sound;
  (iii) a third neural stimulus based on taste;
  (iv) a fourth neural stimulus based on touch; and
  (v) a fifth neural stimulus based on vision;
(c) collecting ultrasound data for the brain while the subject is in the stimulated state, thereby collecting stimulated data, the stimulated data including ultrasound data for one or more second sample volumes within the brain of the subject while the subject is in the stimulated state, the one or more second sample volumes spatially corresponding to the one or more first sample volumes;
(d) comparing the collected relaxed data to the collected stimulated data, wherein comparing the collected relaxed data to the collected stimulated data includes comparing information indicative of tissue displacement in the one or more first sample volumes with information indicative of tissue displacement in the spatially corresponding one or more second sample volumes;
(e) identifying, based on the comparison of the collected relaxed data to the collected stimulated data, at least one of (i) tissue displacement in at least one of the one or more second sample volumes within the brain of the subject associated with the inducement of the neural stimulus and (ii) tissue strain in at least one of the one or more second sample volumes within the brain of the subject associated with the inducement of the neural stimulus, the identified at least one of tissue displacement and tissue strain being present in the collected stimulated data and absent from the collected relaxed data; and
(f) correlating the stimulus with a specific structure in the brain using the identified at least one of tissue displacement and tissue strain present in the collected stimulated data and absent from the collected relaxed data.

22. The method of claim 21, wherein at least one of the steps of collecting the relaxed data and collecting the stimulated data comprises the step of collecting ultrasound data through a portion of a skull of the subject that is not an acoustic window.

23. The method of claim 21, further comprising the steps of:
  (a) collecting cardiac cycle data from the subject; and
  (b) using the cardiac cycle data to re-sample the relaxed data and the stimulated data before the stimulus is correlated with the specific structure in the brain.

24. The method of claim 21, further comprising the step of processing the relaxed data and the stimulated data to prepare the relaxed data and the stimulated data for analysis by filtering out a respiratory signal portion of the relaxed data and the stimulated data.

25. The method of claim 21, further comprising the step of processing the relaxed data and the stimulated data to prepare the relaxed data and the stimulated data for analysis by implementing waveform segmentation, waveform re-sampling, and waveform tapering of the relaxed data and the stimulated data.

26. The method of claim 21, further comprising the step of performing a principal component analysis.

27. The method of claim 26, further comprising the step of performing a one-way multivariate analysis of variance.

28. A system for using at least one of tissue displacement data and tissue strain data acquired by ultrasound for mapping a brain function, comprising:
  (a) an ultrasound component configured to acquire ultrasound data for a brain of a subject;
  (b) a stimulus component configured to induce a neural stimulus in the subject, the stimulus component inducing at least one neural stimulus selected from a group of stimuli consisting of:
    (i) a first neural stimulus based on motion;
    (ii) a second neural stimulus based on sound;
    (iii) a third neural stimulus based on taste;
    (iv) a fourth neural stimulus based on touch; and
    (v) a fifth neural stimulus based on vision;
  (c) at least one controller configured to implement a plurality of functions including:
    (i) acquiring the ultrasound data both before and after the neural stimulus is induced in the subject so as to acquire relaxed data before the neural stimulus is induced in the subject and stimulated data after the neural stimulus is induced in the subject, the relaxed data including ultrasound data for one or more first sample volumes within the brain of the subject before the neural stimulus is induced, the stimulated data including ultrasound data for one or more second sample volumes within the brain of the subject after the neural stimulus is induced, the one or more second sample volumes spatially corresponding to the one or more first sample volumes;
    (ii) comparing the acquired relaxed data to the acquired stimulated data,. wherein comparing the collected relaxed data to the collected stimulated data includes comparing information indicative of tissue displacement in the one or more first sample volumes with information indicative of tissue displacement in the spatially corresponding one or more second sample volumes;
    (iii) identifying, based on the comparison of the acquired relaxed data to the acquired stimulated data, at least one of (i) tissue displacement in at least one of the one or more second sample volumes within the brain of the subject associated with the inducement of the neural stimulus and (ii) tissue strain in at least one of the one or more second sample volumes within the brain of the subject associated with the inducement of the neural stimulus, the identified at least one of tissue displacement and tissue strain being present in the collected stimulated data and absent from the collected relaxed data; and
    (iv) correlating the induced neural stimulus with a specific structure in the brain using the identified at least one of tissue displacement and tissue strain present in the acquired stimulated data and absent from the acquired relaxed data.

29. The system of claim 28, further comprising a cardiac component configured to acquire cardiac cycle data for the subject, wherein the at least one controller is configured to use the cardiac cycle data to isolate a cardiac component of the relaxed data and the stimulated data before the induced neural stimulus is correlated with the specific structure in the brain of the subject, and implement at least one function selected from the group consisting of:
  (a) using the cardiac cycle data to synchronize application of the neural stimulus and acquisition of the ultrasound data; and
  (b) using the cardiac cycle data to re-sample the ultrasound data.

30. The system of claim 29, wherein the cardiac cycle component comprises an electrocardiogram (ECG) component configured to acquire ECG data for the subject.

31. The system of claim 28, further comprising an additional controller, wherein at least one of the functions is implemented by the additional controller.

32. The system of claim 28, wherein the at least one controller is configured to process the relaxed data and the stimulated data to prepare the relaxed data and the stimulated data for analysis.

* * * * *